US011420491B2

(12) United States Patent
Sirault et al.

(10) Patent No.: US 11,420,491 B2
(45) Date of Patent: Aug. 23, 2022

(54) PLANT SCANNING VEHICLE

(71) Applicant: COMMONWEALTH SCIENTIFIC AND INDUSTRIAL RESEARCH ORGANISATION, Acton (AU)

(72) Inventors: Xavier Raymond Richard Sirault, Acton (AU); Michael Salim, Acton (AU); Peter Carl Kuffner, Acton (AU); Jose Antonio Jimenez-Berni, Acton (AU); Richard Sulman, Acton (AU)

(73) Assignee: COMMONWEALTH SCIENTIFIC AND INDUSTRIAL RESEARCH ORGANISATION, Acton (AU)

( * ) Notice: Subject to any disclaimer, the term of this patent is extended or adjusted under 35 U.S.C. 154(b) by 360 days.

(21) Appl. No.: 16/647,787

(22) PCT Filed: Aug. 31, 2018

(86) PCT No.: PCT/AU2018/050946
§ 371 (c)(1),
(2) Date: Mar. 16, 2020

(87) PCT Pub. No.: WO2019/056050
PCT Pub. Date: Mar. 28, 2019

(65) Prior Publication Data
US 2020/0215865 A1 Jul. 9, 2020

(30) Foreign Application Priority Data

Sep. 19, 2017 (AU) ................................ 2017903809

(51) Int. Cl.
*B60G 17/015* (2006.01)
*B62D 49/06* (2006.01)
(Continued)

(52) U.S. Cl.
CPC ....... *B60G 17/015* (2013.01); *B62D 49/0607* (2013.01); *B62D 51/04* (2013.01); *G01C 3/08* (2013.01); *G01N 33/0098* (2013.01)

(58) Field of Classification Search
CPC .. B60G 17/015; B62D 49/0607; B62D 51/04; G01C 3/08; G01N 33/0098
See application file for complete search history.

(56) References Cited

U.S. PATENT DOCUMENTS

| 4,977,971 A | 12/1990 | Crane, III et al. |
| 5,039,129 A * | 8/1991 | Balmer .................... B60G 3/04 |
| | | 180/209 |

(Continued)

FOREIGN PATENT DOCUMENTS

| CN | 210626655 U * | 5/2020 |
| CN | 215836720 U * | 2/2022 |

(Continued)

OTHER PUBLICATIONS

International Search Report dated Nov. 27, 2018 in connection with PCT/AU2018/050946, filed Aug. 31, 2018.

(Continued)

*Primary Examiner* — Faye M Fleming
(74) *Attorney, Agent, or Firm* — Paul Teng

(57) ABSTRACT

Plant scanning vehicles (10) including, but not limited to, plant scanning vehicles for use in field-based phenotyping. There is a central body (16); three or more legs (15) extending from the central body (16) to support a wheel (13) on each leg (15); wherein the three or more legs (15) are mounted to the central body (16) rotatably about a respective vertical axis (95) to allow adjustment of a track width W of the vehicle by rotating the legs wherein the legs are mechanically coupled to transmit rotation between the legs about their respective vertical axes and the central body (16)

(Continued)

or the three or more legs (13) are configured to support a sensor (47) to scan plants.

20 Claims, 18 Drawing Sheets

(51) Int. Cl.
  *B62D 51/04* (2006.01)
  *G01C 3/08* (2006.01)
  *G01N 33/00* (2006.01)

(56) References Cited

U.S. PATENT DOCUMENTS

| | | | |
|---|---|---|---|
| 6,311,795 B1 | 11/2001 | Skotnikov et al. | |
| 6,444,975 B1 | 9/2002 | Reusch | |
| 9,075,698 B2* | 7/2015 | Stachon | A01G 7/00 |
| 10,556,476 B2* | 2/2020 | Dames | B60G 7/001 |
| 2011/0041399 A1 | 2/2011 | Stachon et al. | |
| 2011/0148053 A1* | 6/2011 | Motebennur | B62D 49/0678 |
| | | | 280/6.16 |
| 2015/0015697 A1 | 1/2015 | Redden et al. | |
| 2015/0259185 A1 | 9/2015 | Ditty | |
| 2020/0163269 A1* | 5/2020 | Crowley | B60B 35/109 |
| 2021/0045379 A1* | 2/2021 | Grant | A01M 7/0089 |
| 2021/0245821 A1* | 8/2021 | Crouzat | B62D 49/0607 |

FOREIGN PATENT DOCUMENTS

| | | | | |
|---|---|---|---|---|
| DE | 102016112292 A1 | * | 1/2018 | A01B 61/00 |
| EP | 2058154 A1 | * | 5/2009 | B60B 35/001 |
| FR | 2329501 A | * | 7/1977 | B62D 49/0607 |
| FR | 2673592 A1 | * | 9/1992 | B62D 49/0607 |
| FR | 3016675 | | 11/2016 | |
| GB | 2402658 A | | 12/2004 | |
| WO | WO2010/126879 A1 | | 11/2010 | |
| WO | WO2016/025848 A1 | | 2/2016 | |

OTHER PUBLICATIONS

Written Opinion dated Nov. 27, 2018 in connection with PCT/AU2018/050946 filed Aug. 31, 2018.
IP Australia search report for provisional patent application No. 2017903809 filed Sep. 19, 2017.
A. Ruckelshausen et al., "BoniRob: an autonomous field robot platform for individual plant phenotyping", Precision Agriculture, pp. 841-847 (2009).
G.J. Rebetzke et al., "High-throughput phenotyping technologies allow accurate selection of Stay-green", Journal of Experimental Botany. vol. 67, No. 17. pp. 4919-4024 (2016).
D. Deery et al., "Proximal Remote Sensing Buggies and Potential Applications for Field-Based Phenotyping", *Agronomy*, vol. 5, pp. 349-379 (2014).
Supplementary Search Report dated May 14, 2021 in connection with European Patent Application No. 18 85 8234.

* cited by examiner

PLANT SCANNING VEHICLE

TECHNICAL FIELD

The present invention relates to plant scanning vehicles including, but not limited to, plant scanning vehicles for use in field-based phenotyping.

BACKGROUND

Machinery used in agriculture is often designed for heavy work. As a result, machinery is often large, heavy and expensive. However, the requirements for plant scanning are different. Plant scanning refers to the collection of samples along a distance across an area where plants grow, such as along a field or row of plants. The samples may include samples of sensor data, such as plant height using time of flight laser scanners, ultrasound, temperature sensors, moisture, light, air sensors and others. The employed sensors, such as laser scanners, are relatively light weight and the plants are to be scanned at many different locations, which means a plant scanning vehicle should be relatively easy to transport. A plant scanning vehicle is a vehicle that can support scanning of any element of the plant or the plant growing environment. At the same time, it should have a wide track width to be able to straddle typical rows of plants. However, it is difficult to achieve both of these desirable properties at the same time. A need therefore exists for a new and useful vehicle that is robust for use in a crop or field and is easily transportable and adjustable.

SUMMARY

A plant scanning vehicle comprising a central body; three or more legs extending from the central body to support a wheel on each leg; wherein the three or more legs are mounted to the central body rotatably about a respective vertical axis to allow adjustment of a track width of the vehicle by rotating the legs wherein the legs are mechanically coupled to transmit rotation between the legs about their respective vertical axes and the central body or the three or more legs are configured to support a sensor to scan plants.

The legs may be mechanically coupled to maintain symmetry between the wheels and legs of the vehicle, and the body.

The legs are mechanically coupled to cause the legs to rotate about the respective vertical axes by the same angle.

The sensor may be aligned with a centreline of the vehicle, the legs may comprise two front wheels and the legs are mechanically coupled to maintain the alignment of the sensor and the centreline during movement of the two front wheels away from each other or towards each other.

The legs may have proximal ends at the central body and may be coupled via a toothed coupling. Further, the toothed coupling may comprise a curved rack that is attached to the proximal end of each leg.

The three or more legs may support a front wheel and a rear wheel, the front wheel may be connected to the rear wheel by a rigid member of variable length, and reducing the length of the rigid member may reduce the distance between the front wheel and the rear wheel. Further, the rigid member may comprise a first actuator to change the length of the rigid member to thereby adjust the track width. The first actuator may be a worm drive actuator, pneumatic actuator or electric actuator. Adjusting the track width may be by changing the length of the rigid member and may cause rotation of the legs about respective vertical axes and thereby maintains a constant height of the central body.

The legs comprise one or more joints to allow rotation of the legs about a respective horizontal axis to adjust the height of the central body and/or to collapse the vehicle. Further, the second actuators may be acting on the legs for rotating the legs upwardly and downwardly about the joints. Upward rotation of the legs may lower the body and downward rotation of the legs may raise the body. Upward rotation of the legs may move the legs towards a collapsed configuration and downward rotation of the legs may move the legs towards an expanded configuration. The second actuators may be pneumatic struts.

The legs may be formed as parallelograms comprising a pair of parallel rods which connect at one end to the central body and at the other end to the wheels. The second actuators may be connected diagonally across the parallelograms so that contraction of the second actuators may rotate the legs upwardly or downwardly and expansion of the second actuators may rotate the legs in the opposite direction.

An adjustable sensor mount may be provided to mount the sensor to the central body, wherein the sensor mount may be configured to move the sensor in the direction of travel or adjust the height of the sensor or both.

The sensor may be a laser scanner to measure a distance of the plants from the sensor.

The may be provided a rotary encoder applied to the wheels of the vehicle to provide relative location data of the vehicle.

There may be provided a mover to propel the vehicle.

One or more of the wheels may be rotatable about a vertical axis to steer the vehicle.

There may be provided control electronics to determine control signals for actuators based on user input. The user input may indicate a desired height of the central body or a desired track width or both.

A plant scanning vehicle comprises:

a central body to support a sensor to scan plants;

three or more legs extending from the central body to support a wheel on each leg;

the legs are mounted to the central body rotatably about a respective vertical axis to allow adjustment of a track width of the vehicle by pitch rotating the legs wherein the legs are mechanically coupled to transmit pitch rotation between the legs about their respective vertical axes, and the legs comprise one or more joints to allow rotation of the legs about a respective horizontal axis to adjust the height of the central body and/or to collapse the vehicle.

A collapsible vehicle includes:

a body first and second front wheels, first and second rear wheels, four legs, each leg extending from the central body to support a wheel of the first and second front and rear wheels, the legs extending from the central body in a symmetrical configuration about the central body, the legs being rotatable between collapsed and expanded configurations whereby in the collapsed configuration the wheels are proximate the central body and in the expanded configuration the wheels are remote from the central body, the legs being connected mechanically to each other such that: rotation of one of the legs between the collapsed and expanded configurations results in the same extent of rotation of the other legs between the collapsed and expanded configurations, and the symmetrical configuration of the legs about the body is maintained during rotation of the legs between the collapsed and expanded configurations.

A collapsible vehicle for use in field based phenotyping includes:
a central body
first and second front wheels,
first and second rear wheels,
four legs, each leg extending from the central body to support a wheel of the first and second front and rear wheels, the legs extending from the central body in a symmetrical configuration about the central body,
the legs being rotatable between collapsed and expanded configurations whereby in the collapsed configuration the wheels are proximate the central body and in the expanded configuration the wheels are remote from the central body, A collapsible vehicle includes:
a body
first and second front wheels,
first and second rear wheels,
four legs, each leg being connected to and extending from the body to support a wheel of the first and second front and rear wheels, the legs extending from the body in a symmetrical configuration about the body,
the legs being rotatable between collapsed and expanded configurations whereby in the collapsed configuration the wheels are proximate the body and in the expanded configuration the wheels are remote from the body,
the vehicle further including actuators acting on the legs for rotating the legs upwardly and downwardly about the connections to the body so that the body can be lowered by upward rotation of the legs and raised by downward rotation of the legs,
and whereby during rotation of the legs towards the collapsed configuration the legs rotate upwardly about the connections to the central body so that the body lowers as the legs rotate, and whereby during rotation of the legs towards the expanded configuration the legs rotate downwardly about the connections to the central body so that the body rises as the legs rotate.

BRIEF DESCRIPTION OF DRAWINGS

In order that the invention may be more fully understood, some embodiments will now be described with reference to the figures in which:

FIG. 17a illustrates a vehicle configuration where the central body is lowered to scan smaller plants while

DESCRIPTION OF EMBODIMENTS

Figure 1:
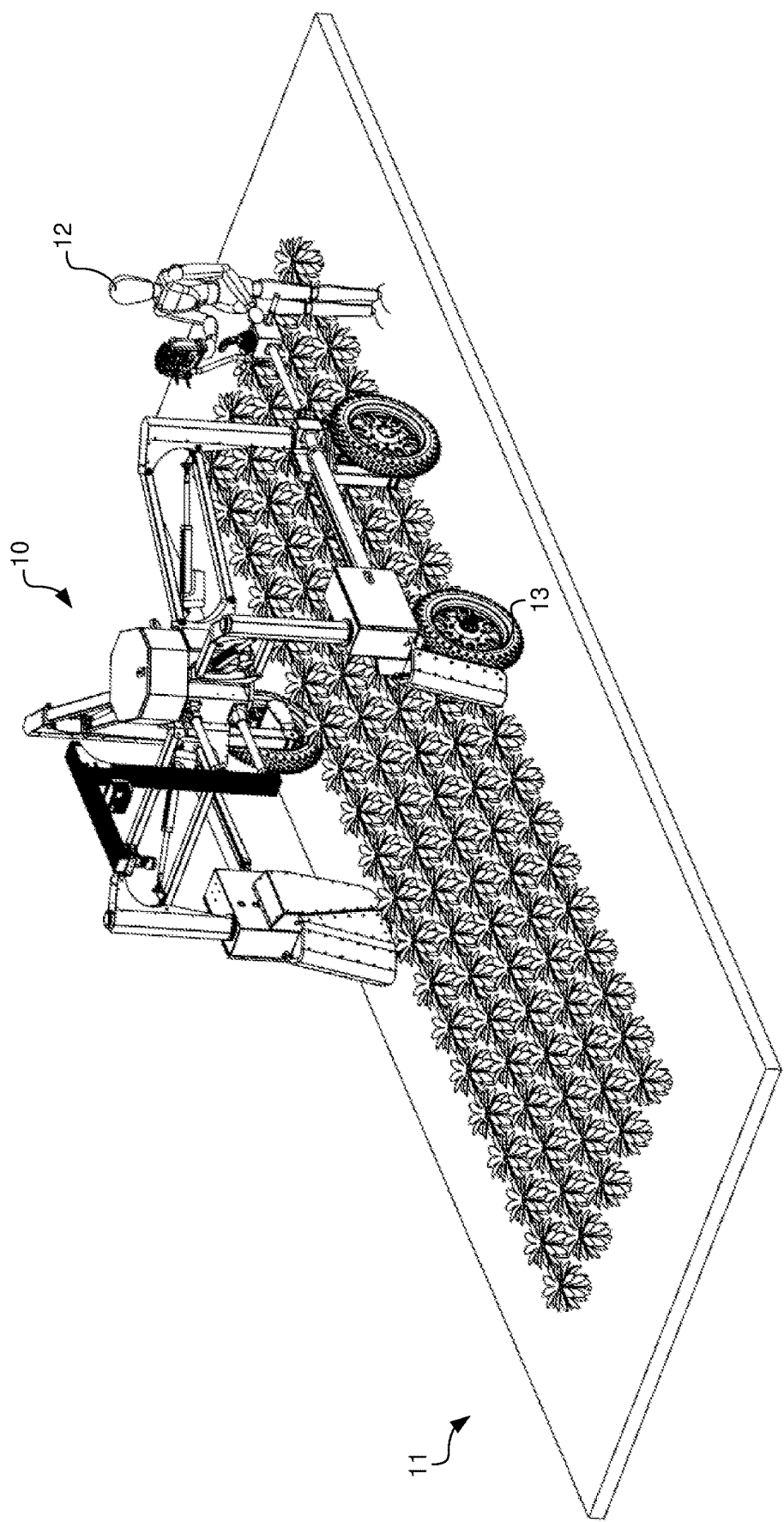
FIG. 1 is a perspective view of a collapsible vehicle shown in field-based plant scanning according to one form of the invention.

FIG. 1 is a perspective view of a foldable or collapsible vehicle 10 that has been constructed for the purpose of field-based plant scanning and which is shown with four wheels straddling plot 11 comprising a generic crop of plants. The vehicle 10 is shown being controlled by a schematic operator 12 such that in FIG. 1, the operator 12 controls the speed and direction of the vehicle 10 and walks with the vehicle 10 as it progresses along the plot 11. In other embodiments, the operator may be remotely controlling the vehicle using a video link, for example, or the vehicle may be autonomous using the various sensors discussed herein as navigation inputs.

Vehicle 10 has wheels 13 that are positioned on either side of the plot 11. Plot 11 is shown as a crop row which would form one of a plurality of crop rows that are spaced apart by a spacing row. The width between the wheels 13 of the vehicle 10 is adjustable and therefore selected so that the wheels travel along the spacing between adjacent crop rows. In one example, the operator 12 selects the width of the vehicle 10 through input means, such as buttons or a touch screen. In other examples, the vehicle detects gaps between plant rows, such as by using a camera image or laser scanning data, and adjusts the width automatically to fit into those gaps.

Figure 2:
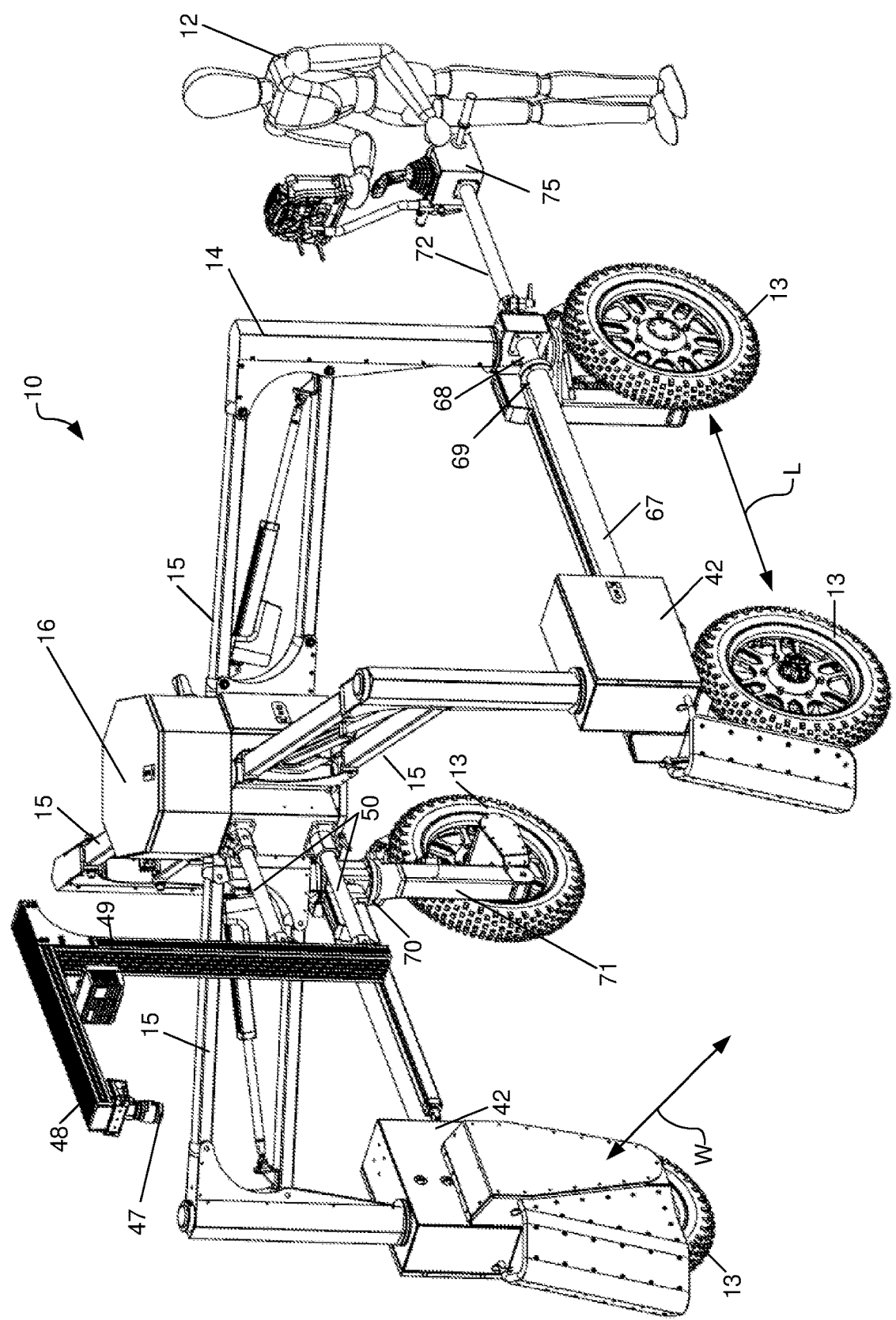
FIG. 2 is a perspective view of the collapsible vehicle of FIG. 1.

FIG. 2 illustrates the vehicle 10 in isolation from the plot 11 and that figure shows that the four wheels 13 of the vehicle 10 are indirectly connected to a vertical post 14 which connects to a four-point articulated leg 15. The leg 15 connects between the post 14 and a central body (also referred to as "housing" or "hub") 16. It is noted that "central" in relation to the body does not mean that the body 16 is exactly at the centre of the vehicle but means that the body 16 is within the perimeter defined by the wheels. In other words, central body 16 is between the wheels and may be off-axis resulting in an asymmetrical set-up. The central hub 16 is illustrated in isolation in FIG. 3 and this shows that the central hub 16 has an upper structural enclosure 18 and a lower structural body 19. The upper structural enclosure 18 is provided for housing relevant instrumentation and operating controls, while the lower structural body 19 includes fittings for connecting structural members of the vehicle 10 to the central hub 16, such as bearings to receive post 26. The lower structural body 19 also includes storage capacity as shown by the cavity 20 and the door closures 21. The upper enclosure 18 can also be closed by a closure 22.

Figure 3:
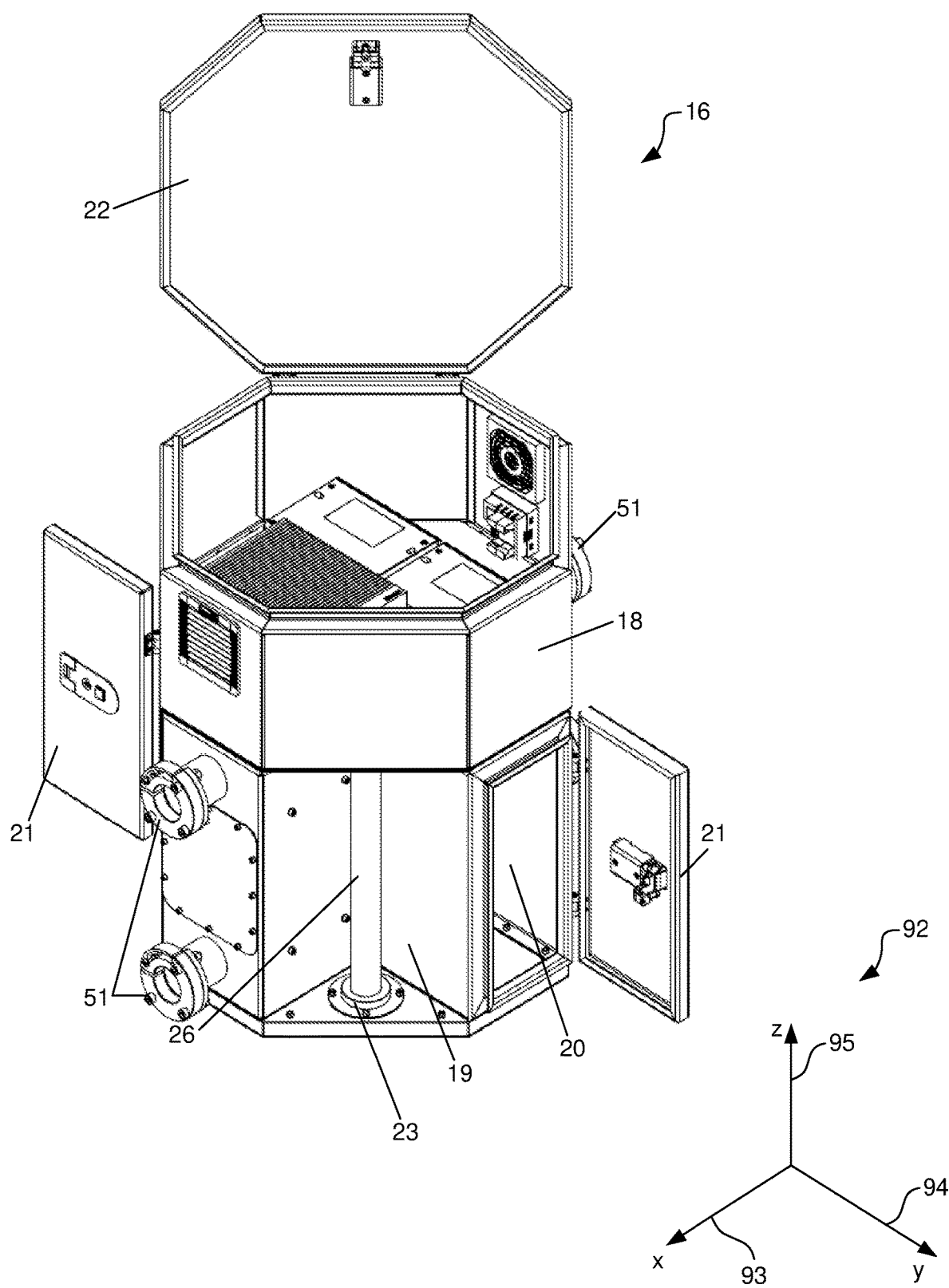
FIG. 3 is a view of the central body of the vehicle of FIG. 2.

The hub 16 is formed as a hexagon, however it could be formed in any suitable shape including square, rectangular and circular. FIG. 3 also shows a coordinate system 92 comprising a horizontal x-axis 93, a horizontal y-axis 94 and vertical z-axis 95. Rotation of leg 15 around the hub 16 about any horizontal axis that lies in the plane of the x- and y-axis is herein referred to as pitch rotation. Rotation around the hub about vertical z-axis 95 is herein referred to as yaw rotation. In FIG. 3 post 26 is mounted to the hub 16 so that it can rotate about z-axis 95. To that end, hub comprises bearings 23 that receive post 26 on both ends of post 26 although the top end of post 26 is obscured by hub 16.

With reference to FIGS. 1 and 2, the legs 15 extend from the hub 16 and specifically from the lower structural body 19 of the hub 16. In the form illustrated, the legs 15 are four point articulated linkages which are shown in more detail in FIG. 4. Each leg 15 thus includes a connecting bracket 25 that connects to a post 26 of the hub 16 (see FIGS. 3 and 8). The bracket 25 includes an opening 27 through which the post 26 can be accommodated. The top of the post 26 extends through the opening 27. It can be seen in FIG. 4 that the bracket 25 is formed from a pair of plates 28 and 29 which bolt together about the post 26.

The leg 15 further includes upper and lower links or struts 30, 31, which are rotatably connected at one end to the bracket 25 about pins 32 and 33 and at the other end to a second bracket 35, about pins 36 and 37. In this sense, pins 32 and 33 act as a joint that allows pitch rotation of legs 15 about a horizontal axis 41 (vertical yaw rotation axis 95 is also shown). The bracket 35 accepts an upper end of a post 14 as shown in FIGS. 1 and 2 and for this, the bracket 35 includes an opening formed in a similar manner to the opening 27 of the bracket 25 and similar to the bracket 25, the bracket 35 includes plates 38 and 39 which are bolted together about the upper end of the post 14. The upper end of the post 14 does not extend through the upper plate 40 but rather, terminates underneath the plate 40 within the bracket 35.

The leg 15 is intended to allow up and down movement, such as vertical movement of the bracket 35 relative to the bracket 25 and that movement is driven by an actuator 45. The actuator 45 may be a hydraulic, diesel, electric or pneumatic actuator 45. Opposite ends of the actuator 45 are connected to diagonally opposite regions of the links 30 and 31 and contraction of the actuator 45 tends to lift the bracket 35 relative to the bracket 25, while extension of the actuator 45 tends to lower the bracket 35 relative to the bracket 25. The contrast between the expanded and contracted conditions of the actuator 45 are shown in the relative positions of the wheels 14 as shown in FIGS. 1 and 2 when compared to FIG. 5. Actuator 45 can be of any suitable form and can include linear actuators and/or screw actuators such as ball screws, or pneumatic or hydraulic struts. The actuator 45 effects a pitch rotation of the leg about bracket 25 within a maximum and minimum configuration. The minimum and maximum configurations correspond to a minimum and maximum height of the vehicle, which, in turn, is defined by the geometries of the parallelograms of the legs 15. The minimum and maximum configurations are those where the space within the parallelogram is just sufficient to accommodate the pneumatic actuator 45. This means that at the maximum configuration/maximum height, the legs extend downwards from hub 16 and hub 16 with bracket 25 is above bracket 35. Alternatively, the actuator 45 and/or a physical stopper may provide a maximum configuration where leg 15 is substantially horizontal.

Figure 5:
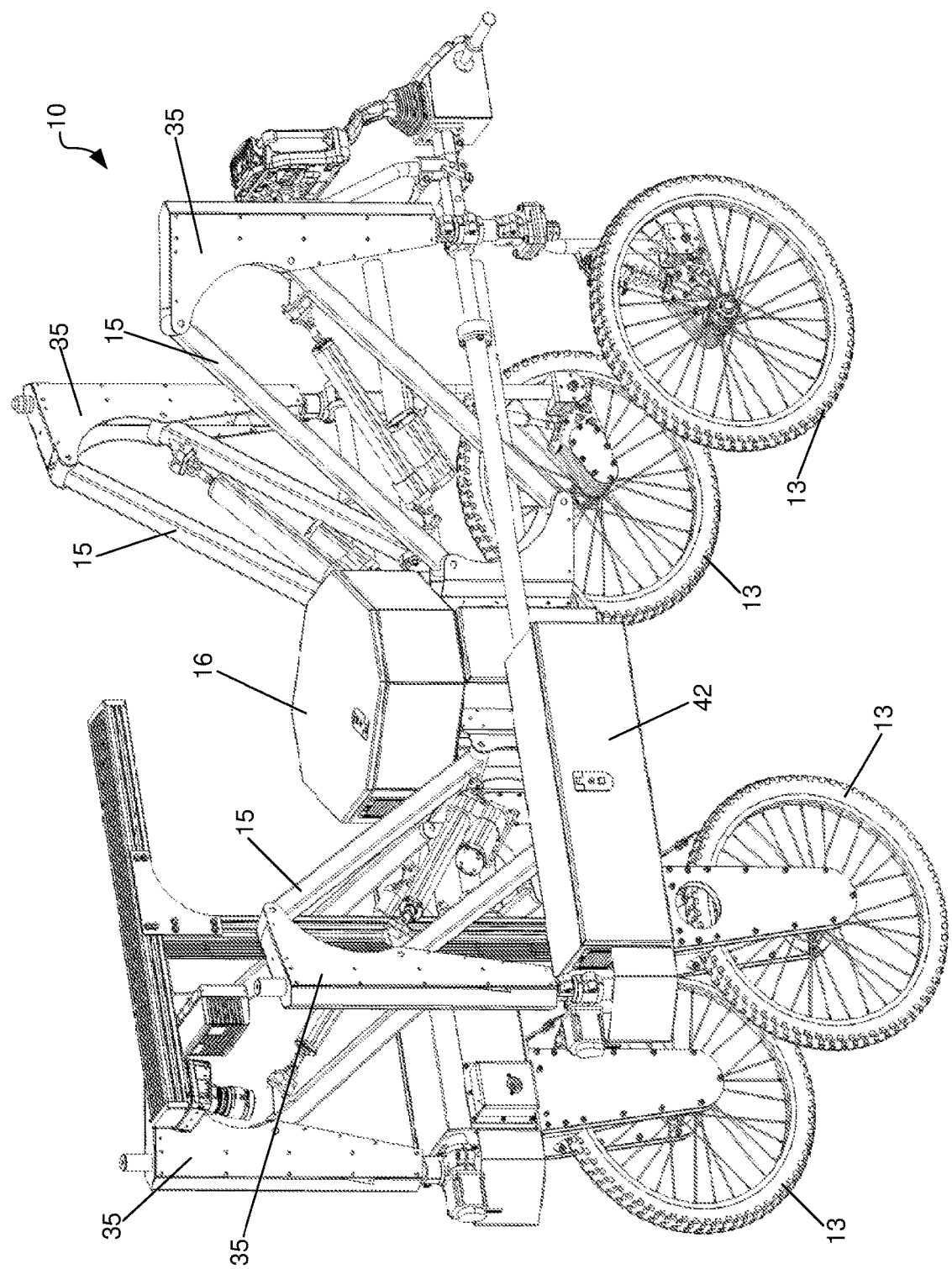
FIG. 5 is a perspective view of the vehicle of FIG. 2 in a collapsed configuration.

In FIG. 5, it is evident that the legs 15 have each rotated upwardly relative to the brackets 25 so that the brackets 35 are positioned above the brackets 25. By that pitch rotation, the track width W as shown in FIG. 2 has been reduced, as has the lengthwise spacing L between respective front and rear wheels 13. This results in the wheels 13 moving closer to the central hub 16. In one embodiment, a maximum track width of about 2.8 metres can be reduced to a track width of about 1.5 metres by rotating legs 15 from the most extended to their most retracted configurations via this pitch rotation. Moreover, the longitudinal or lengthwise centre spacing between front and rear wheels (wheelbase) can be reduced from a maximum of 2.8 metres down to a minimum spacing of 1.5 metres and is relative to the length of leg 15. It is noted that the pitch of legs 15 can be adjusted across the entire range between collapsed and expanded configurations at a constant yaw. This generally coincides with an extension or contraction of rod 67/68. However, it is not material whether the yaw changes or remains constant to the functioning of the mechanism.

Figure 10B:
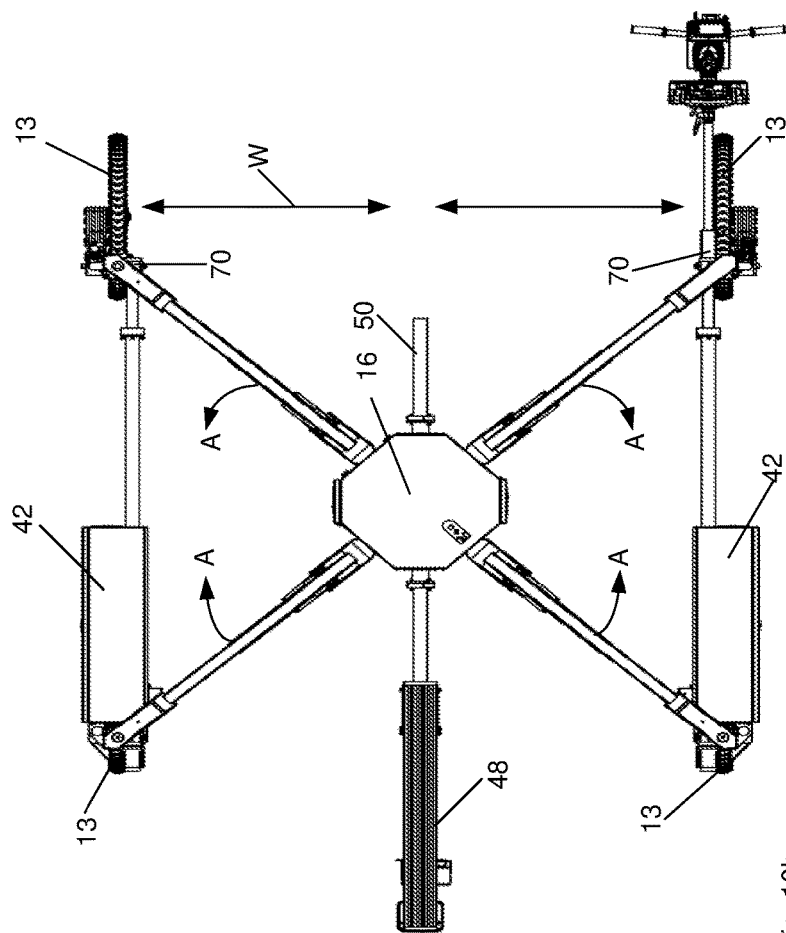
FIGS. 10a and 10b are plan views of the vehicle of FIG. 2 in collapsed and expanded configurations respectively.
Figure 10C:
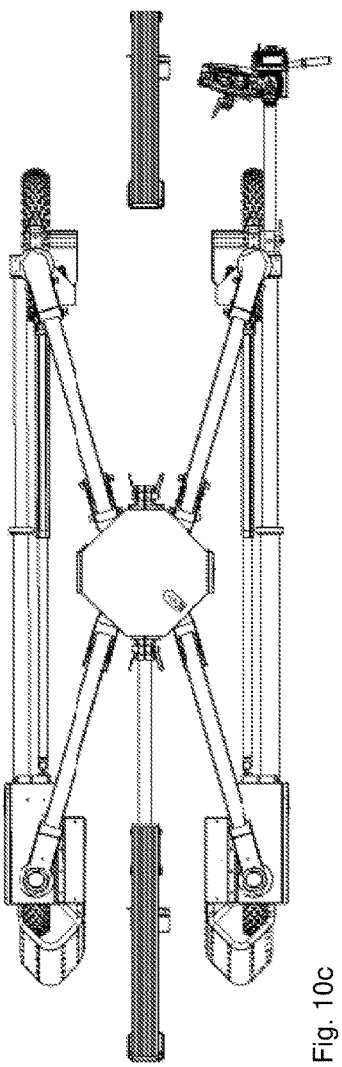
FIG. 10c is a plan view of the vehicle in a maximum length and minimum width configuration.

It is to be noted that the spacing shown in FIGS. 1 and 2 is not the maximum spacing of the wheels 13. The maximum spacing is shown in FIG. 10b. The minimum spacing is as shown in FIG. 5. It is noted that a different minimum and maximum spacing may equally be possible. In particular, for larger scale agricultural settings, the vehicle may fold to a maximum of 3.3 metres and may be towed behind a tractor or other mover. The frame folding geometry lends itself to scalability. In one example, vehicle 10 is a transportable autonomous vehicle that is used for scanning of crops or other functions that uses a maximum wheel track of 3 m or more to suit current tractor spacing, but needs to fold up to below the road legal width of 2.4 m. A scaled version of vehicle 10 could achieve that. Further, it is also possible to scale down and make smaller versions for other applications.

The mechanism for folding or collapsing the vehicle 10 between the operating position of FIGS. 1 and 2, to the fully collapsed or folded position of FIG. 5, will be described in more detail later herein, but one aspect of the mechanism is for the actuators 45 to contract, thereby commencing lifting movement from the positions illustrated in FIGS. 1 and 2 to elevate the bracket 35 to the positions illustrated in FIG. 5. The operating position is the position at which the vehicle operates for a particular application and would typically not change during the movement across the plants. The operating position may be a position of maximum height of hub 16 or a position where legs 15 are horizontal. It is noted, however, that any position including positions where the legs 15 are extended below or above the horizontal, can be considered operating positions. Extending legs 15 to a horizontal operating position has the advantage that a change in the height of hub 15 to adjust for different crop heights does lead to only a small change in track width (according to the cosine of the pitch angle). It is noted that changing the height of hub 15 by changing the length of actuators 45 (see FIG. 4) without rotating the legs 15 about their respective axes 95 would result in a change of width. However, the hub height can be changed at constant width by changing the length of actuators 45 at the same time as rotating the legs 15 accordingly. This "mixing" of control channels may be programmed into a microcontroller to occur automatically when a user changes the height through a user input.

Figure 17A:
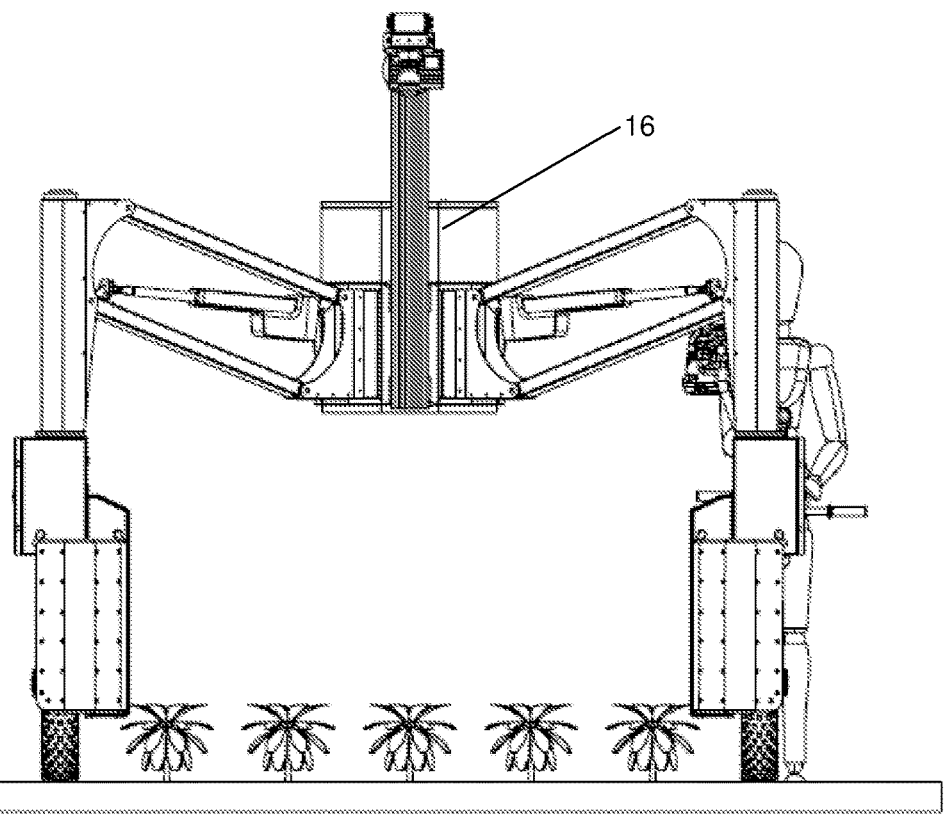
Figure 17B:
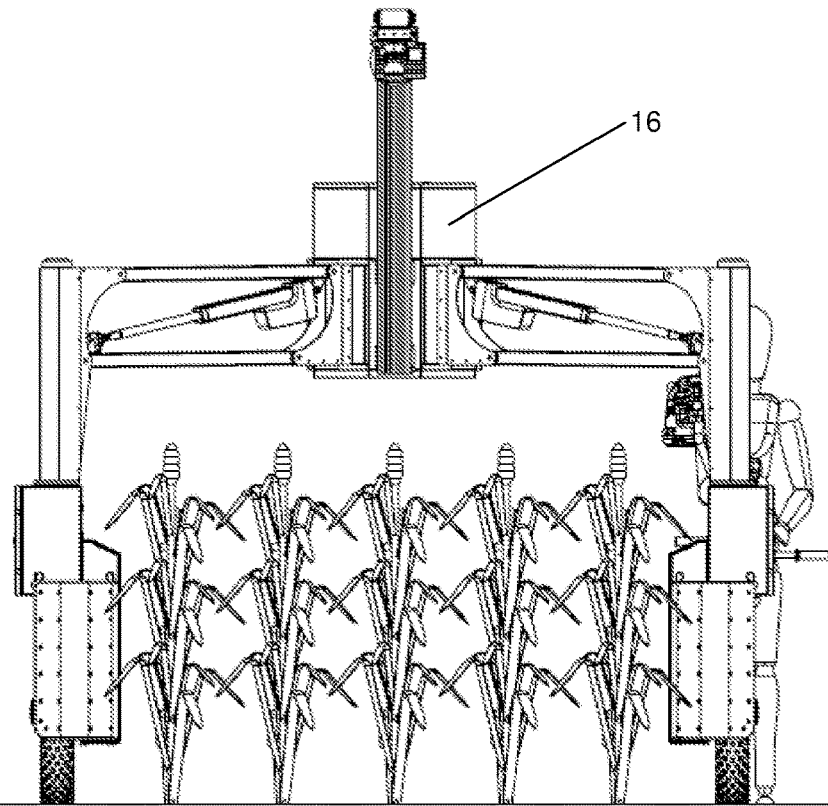
FIG. 17b illustrates a vehicle configuration where the central body is raised to scan larger plants.

FIGS. 17a and 17b illustrates one example. FIG. 17a illustrates a vehicle configuration where the central body 16 is lowered to scan smaller plants while FIG. 17b illustrates a vehicle configuration where the central body 16 is raised to scan larger plants. It is noted that the distance between the wheels is kept constant in this example.

In the arrangement illustrated in FIG. 5, collapsing movement can be accompanied by rolling movement of the vehicle along a ground surface to avoid sideways slippage of wheels 13.

It will be apparent from the figures that the vehicle 10 can be expanded to the configuration of FIGS. 1 and 2, or to the maximum configuration of FIG. 10b and can be collapsed or folded to the minimum configuration of FIG. 5. However, it is also possible for the vehicle 10 to adopt an infinite number of positions intermediate the maximum and minimum configurations. This adjustment is simple and quick by actuation of the actuators 45 and can be completed as the vehicle 10 is in motion once the rod 67/68 is released to allow it to contract as needed. Practically, the smallest configuration is achieved when rod 67/68 is contracted as far as possible and pneumatic actuators are also contracted as far as possible. The yaw angle is then fully defined by the geometries of the components.

In addition, a major advantage of the present invention can be achieved by controlling the actuators 45 so that the vehicle maintains symmetry between the wheels 13 and the hub 16. This enables the position of the sensors that the vehicle 10 carries to have a constant repeatable relationship between other parts of the vehicle 10, such as the wheels 13 and the hub 16. For example, the figures show a sensor 47 which is fixed to a sensor leg 48 that connects to a post 49 from which rails 50 extend. The rails 50 extend through slide tubes 51 of the hub 16 (see FIG. 3). The slide tubes 51 extend from one side of the hub 16 to the other so that the position of the sensor 47 can be adjusted forward and back relative to the hub 16. Likewise, the height of the sensor 47 can be adjusted as will be described later herein. However, the advantage that can be provided by the vehicle 10 and the manner in which it folds, is that as the wheels 13 can be controlled to move towards the hub 16 to reduce the spacing W and L of FIG. 2, the relative spacing between a wheel 13 on one side of the hub 16 wheels 13 and the sensor 47 remains the same as the spacing between the opposite wheel 13 and the sensor 47. It therefore follows that under equal expansion or contraction of actuators 45, no matter what the spacing W between the front wheels 13 and the rear wheels 13, the sensor 47 will always be positioned midway between them. This is evident from FIGS. 6a and 6b whereby a vertical centreline taken from the sensor 47 intersects a horizontal line made between the pair of front wheels 13 such that the spacing W1 between first of the wheels 13 and the centre line is equal to W2 between the second of the wheels 13 and the centre line. Likewise, when the vehicle 10 is completely collapsed, W3 is equal to W4. It will be evident that at any point between the positions shown in FIGS. 6a and 6b, there will be an equal spacing between the wheels 13 on either side of a vertical centre line through the sensor 47. The advantage is that sensor recalibration is not required for the entire sensing equipment each time a movement or adjustment is made to the vehicle.

As an example, where a sensor is disposed on a centreline between the front wheels, symmetrical movement of the front wheels away from each other or towards each other maintains the sensor on the same sensor lines. That is, the centreline between the wheels does not shift because the wheels are shifted outwardly or inwardly relative to each other an equal distance at every movement. Encoders that might be positioned on the front wheels might move towards and away from the centre line on which the sensor is disposed, but the distance of the wheels will always be equal on either side of the centre line. It is noted that examples herein relate to sensors being attached centrally to leg 48 but it would be apparent to a person skilled in the art that the sensors may be mounted to the vehicle 10 anywhere. Hub 16 is configured to support a sensor in the sense that the sensors may be attached to the hub in various different ways, including legs, gantries, booms, ropes, rigs, and other structures.

Figure 18:
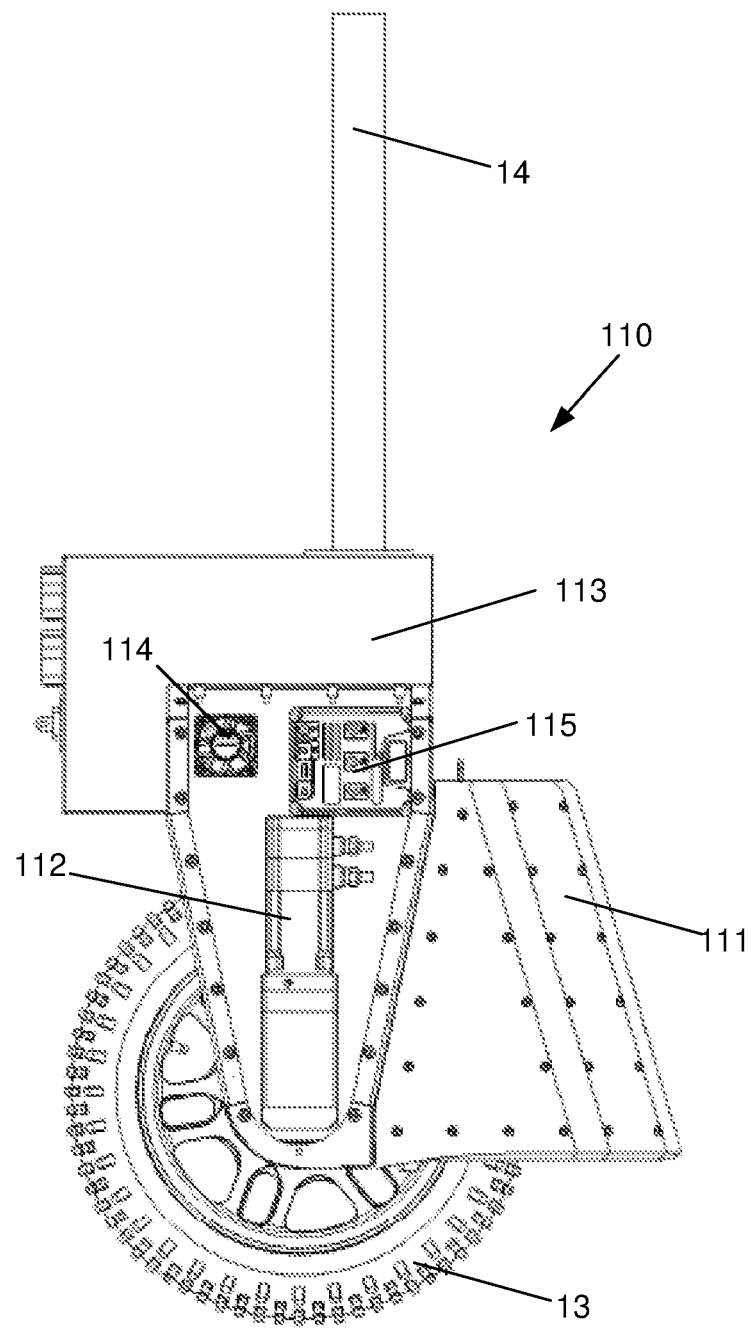
FIG. 18 shows one of the wheels in more detail.

FIG. 18 shows one of the wheels 13 in more detail. In this case, one of the front wheels is shown. The wheel 13 is mounted on a wheel support 110 comprises a post 14 that is received by one of the legs 15 (not shown in FIG. 18). Wheel support 110 also comprises a wheel guard 111 to guide sideward branches or stalks away from the wheels to reduce damage to the plants. There is also a suspension element 112, such as a gas spring, to provide for a smooth ride across the field. Wheel support 110 further comprises an electronics compartment 113 cooled by a fan 114. On the outside of the electronics compartment 113, there are sensors 115. In this example, the sensors 115 are directed inwardly, that is, towards the other front wheel. There may also be matching sensors mounted on the other front wheel. For example, there may be a vertical array of LEDs on one front wheel and an array of photodiodes on the other front wheel to form a light curtain that measures crop height by detecting which light paths are covered by the plants. Other sensors may equally be provided and they may measure the distance between the wheels for automatic configuration of the vehicle.

Figure 4:
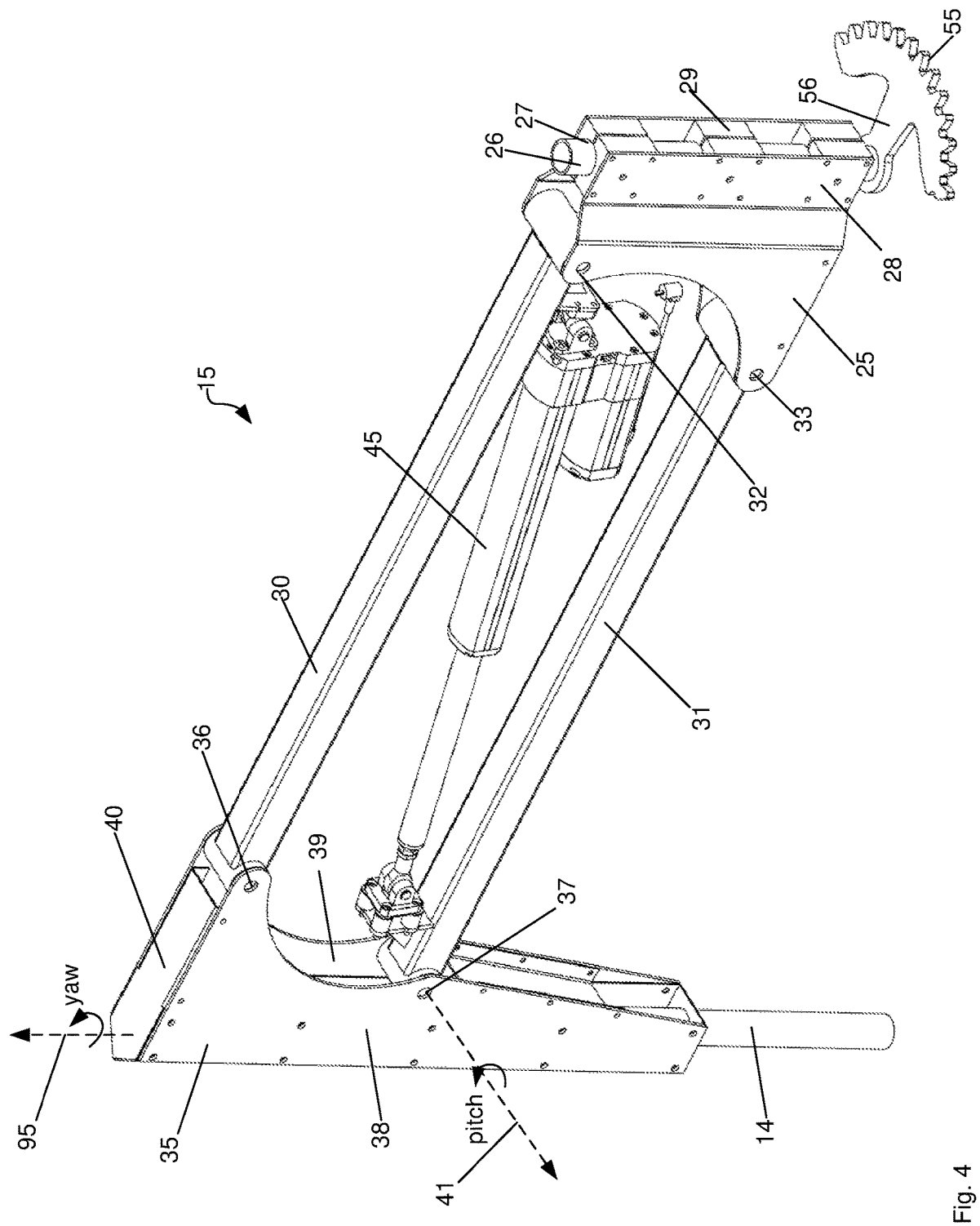
FIG. 4 is a perspective view of a leg of the vehicle of FIG. 2.
Figure 6A:
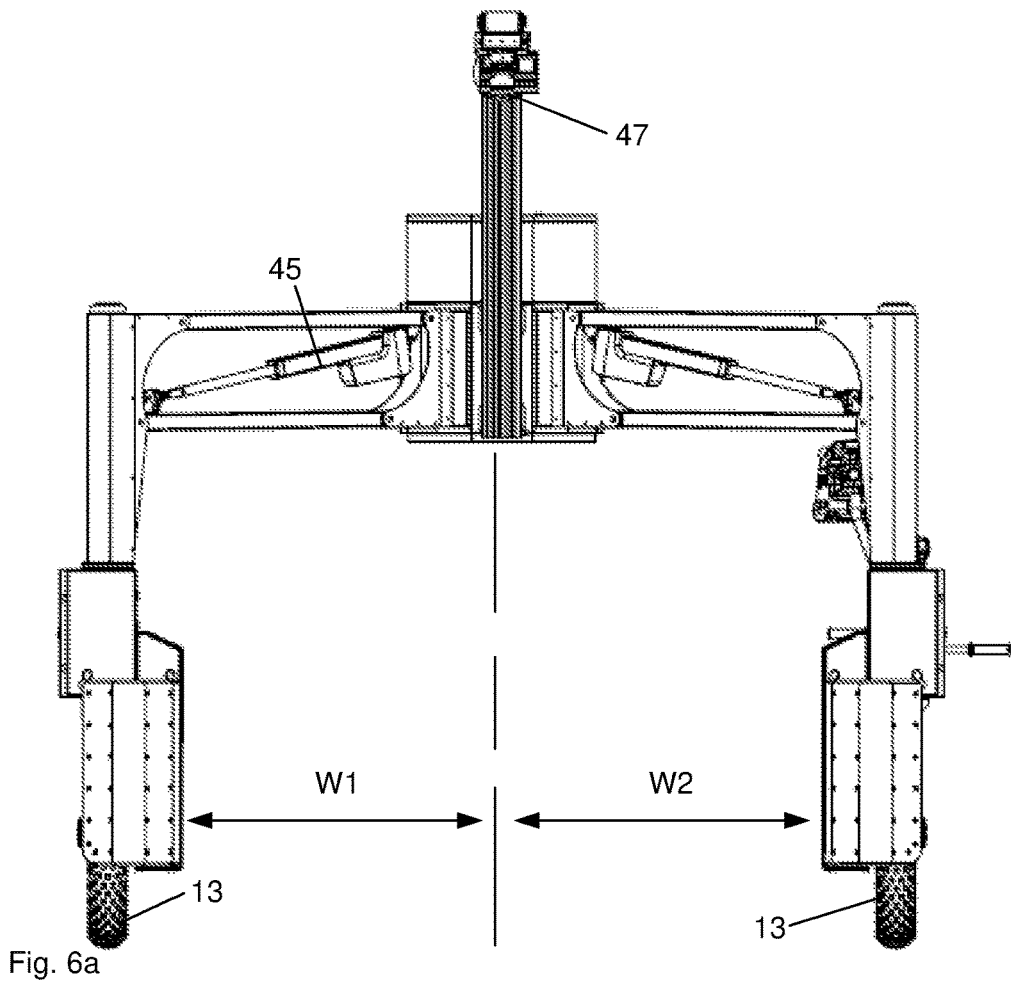
FIGS. 6a and 6b are end views of the vehicle of FIG. 2 in expanded and collapsed configurations respectively.

As described above, rotation of legs 15 about respective horizontal axes, as defined by pins 36,37 acting as pivoting joints in FIG. 4, cause the wheels 13 to move towards or away from hub 16. At the same time, hub 16 moves up or down. In one way of using vehicle 10, operator 12 unloads the collapsed vehicle and expands vehicle 10 by controlling the expansion of actuators 45 until vehicle 10 is unfolded. For example, operator 12 stops the rotation of legs 15 when they are about horizontal as shown in FIG. 6a. Operator 12 can then fine-tune the rotation of the legs to adjust the height of hub 16 to a desired height. This desired height may depend on the type of crop that is to be scanned or the type of scanning to be performed. Therefore, the set height of hub 16 may not change during the progress of the scan. In other examples, the height of hub 16 remains constant in a position where the legs are horizontal and pneumatic actuators 45 are only activated when the vehicle is collapsed.

However, the width of the row may change as the scan progresses. Further, different plots of different widths are scannable with the vehicle while maintaining consistency with other settings, such as height of hub 16. Therefore, it is important in those circumstances that the track width can be changed without changing the height of hub 16. In particular, if sensor 47 is a distance sensor, such as a laser rangefinder, it is important not to change the height of the sensor 47 because changing the height of sensor 47 would change the sensed crop height, which may make the measurements inconsistent.

Figure 7:
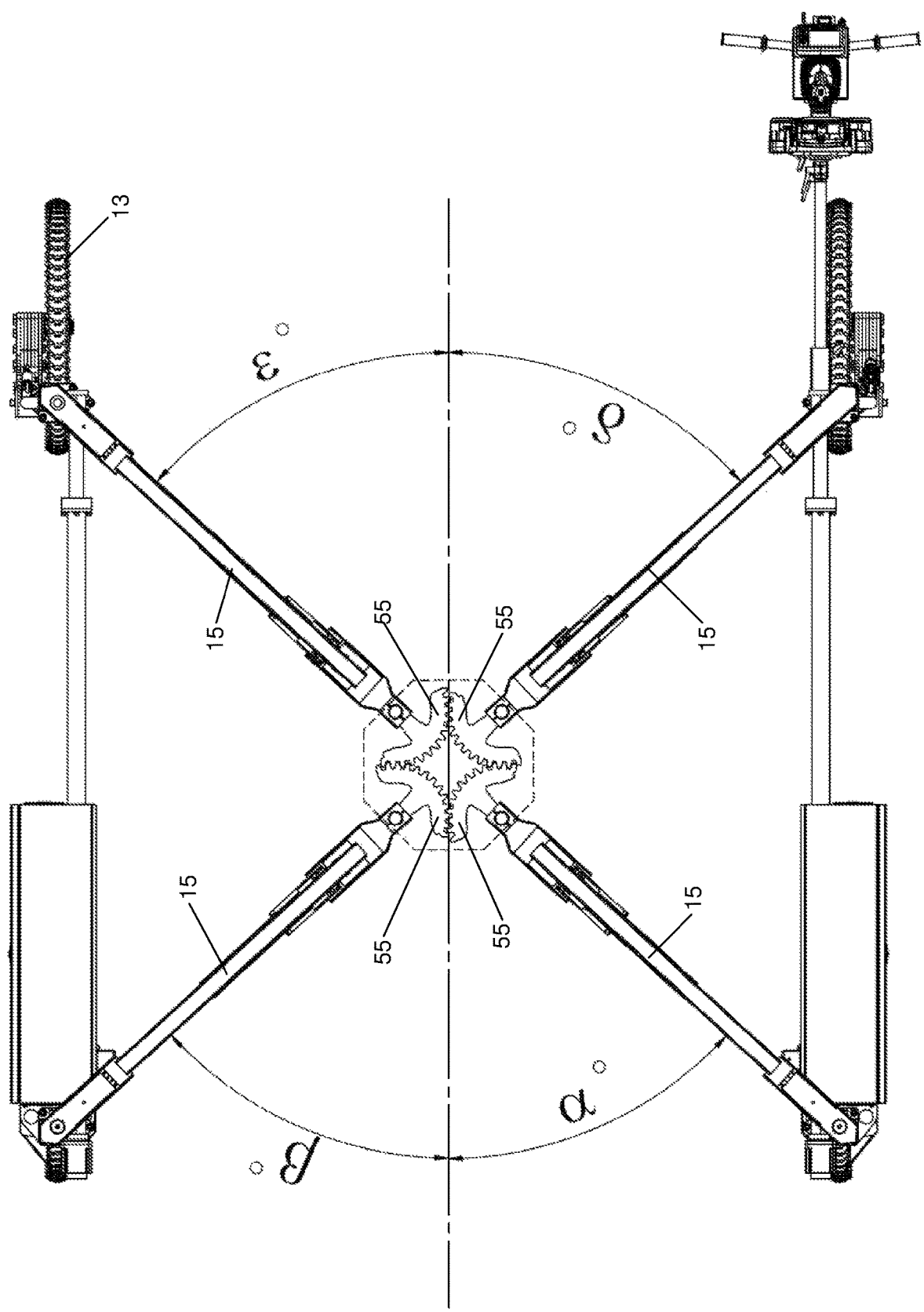
FIG. 7 is a plan view showing leg connections of the vehicle of FIG. 2.
Figure 8:
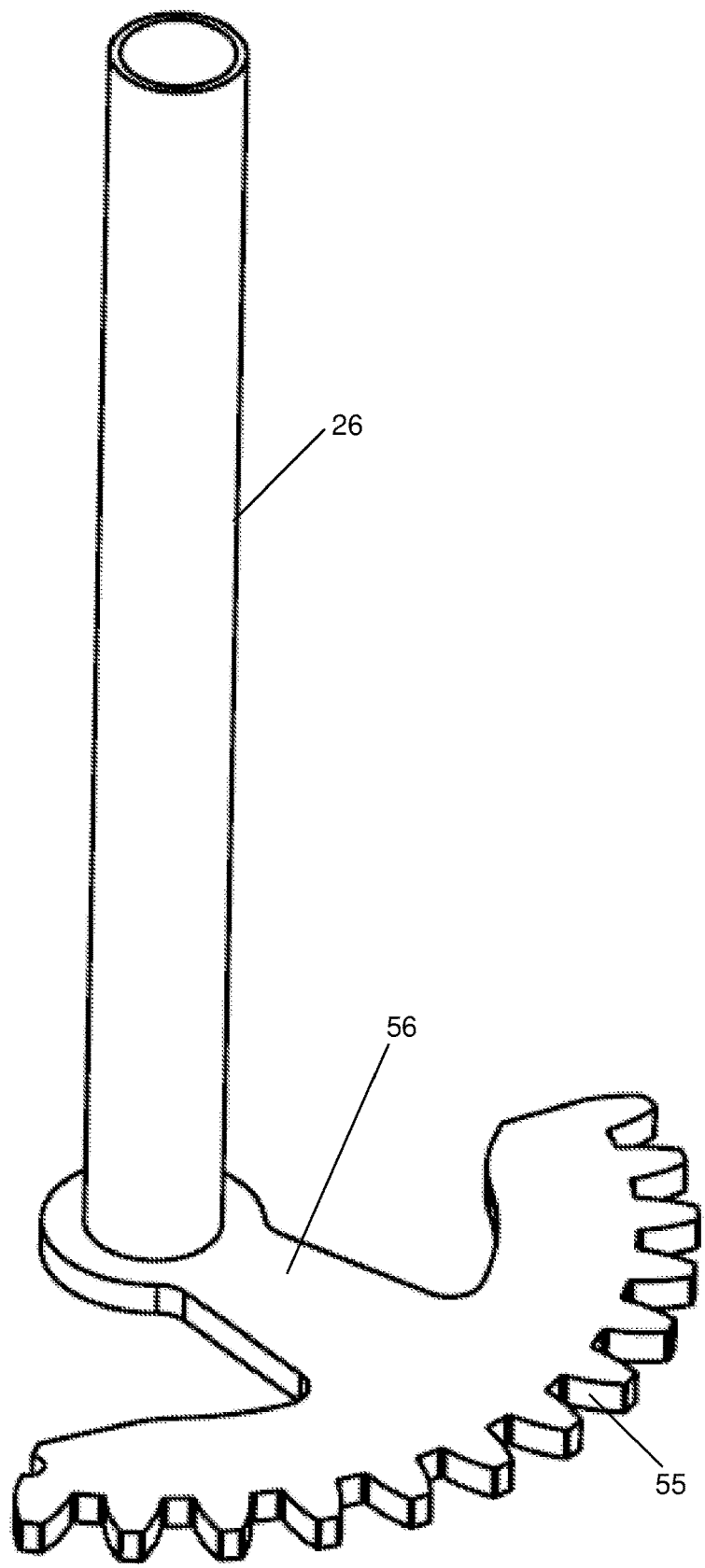
FIG. 8 is a view of the curved toothed rack of FIG. 7.

FIG. 7 shows an example of how adjustment of track width can be achieved while maintaining a constant sensor height. The discussion of FIG. 7 will take place with further discussion in relation to FIGS. 4 and 8. In FIG. 4, the upper end of the post 26 is shown projecting out of the opening 27 and the post 26 is also shown in FIG. 3 installed within the lower structural body 19 of the hub 16. Not shown in FIG. 3 is a gear 55 which is shown in FIGS. 4, 7 and 8. Gear 55 is not shown because it is located at the underside of hub 16 and therefore obscured. FIGS. 4, 7 and 8 show that the gear 55 is connected to a bottom end of the post 26 and is formed as a curved toothed rack comprising a plurality of gear teeth, and also includes a stem 56 to connect to the post 26. It is noted that gear 55 may equally be connected to the top end of post 26. However, having gear 55 connected to the bottom of post 26 has the advantage that the gear 55 can be located at the underside and outside the lower structural body 19 which means that no additional openings are required in lower structural body 19 to receive gears 55. Gears 55 may be protected by another steel plate underneath the gears and a rubber seal located between the steel plate and the underside of structural body 19 and surrounding the gears 55.

Each of the legs 15 includes a gear 55. As shown in FIG. 7, in the assembled arrangement of the vehicle 10, the respective gears 55 mesh centrally of the hub 16. As is evident from FIG. 7, each gear 55 is directly meshed with a further two of the gears 55. Moreover, because the posts 26 to which the gears 55 are connected are rotatably mounted to the hub 16, rotation of one of legs 15 results in rotation of the other three legs 15 by virtue of the meshed gearing between the gears 55. It follows that in relation to FIG. 7, the respective angles shown in that figure will remain equal upon rotation of the legs 15. That is, in the arrangement shown, $\alpha=\beta=\varepsilon=\delta$ always. This is because the legs 15 are physically constrained to retain the angularity between them by virtue of the geared arrangement that transmits yaw rotation between the legs. In other words, the mechanical coupling in form of the curved toothed rack 55 transmits yaw rotation of one of the legs to all the other legs. Thus, it is not possible in the arrangement of the vehicle 10 to move one of the legs 15 without movement of the other legs 15, nor is it possible for one of the legs 15 to be moved to alter the constant angular relationship that is illustrated in FIG. 7. Maintaining the relative geometry of the components of the vehicle allows the wheels of the vehicle to be moved to increase or decrease track width without requiring recalibration of the entire sensing equipment each time a movement or adjustment is made. That is, because symmetry is maintained, the relative position of the encoder mounted on the wheels and the sensors on the body will be known despite the position of the wheels being adjusted. That retention of symmetry means that the ratio of the spacing between sensors and wheels is maintained even though the actual distances or spacing might vary. It is noted that the encoder and sensors can be mounted anywhere on the vehicle 10. In some examples, there is a constant relationship between the locations of the encoder and sensors to simplify the accurate location tagging of sensor data.

In one form, inner ends of the legs 15 are connected via a toothed connection that can comprise a curved rack 55, for example, that is attached to each leg 15. In this form, the inner ends of the legs extend to a position proximate each other whereby curved toothed racks 55 associated with each inner end engage and whereby yaw rotation of one leg 15 rotates the curved toothed rack 55 associated with that leg, transmits the yaw rotation to the other legs and thus causes the yaw rotation of the other legs also. It is noted that one connection between the curved toothed rack 55 in FIG. 7 can be opened while retaining the overall functionality. For example, the connection between angles $\varepsilon$ and $\delta$ can be opened and the transmission of yaw rotation is retained if the other three connections are kept. Alternatively, each curved toothed rack can be in contact with two curved toothed racks, as depicted in FIG. 7. This latter arrangement provides a compact arrangement that has good stability given that each curved toothed rack has two points of connection. By this arrangement, yaw rotation of one leg through a set angle causes the same amount of rotation of the other legs. It follows that if a drive is provided to rotate the legs, only a single drive is required. Alternatively, if the legs are rotated manually, movement of one leg causes movement of the three other legs. In one example, there are two legs that are not connected via the mechanical coupling. Since those two legs are still indirectly coupled via the coupling to the other legs, this mechanical system is still fully determined.

The arrangement of FIG. 7 is a mechanical connection or coupling between the legs 15 and ensures that the legs 15 rotate together and to the same extent whenever rotation of one of the legs is driven. Moreover, the geared connection between the legs allows an infinite variation of the spacing of the wheels between the maximum and minimum configurations achievable by yaw rotation, that is, minimum and maximum length of rod 67/68. It is noted that there are other mechanical couplings that may achieve consistency of positioning between the sensor 47 and the wheels 13 while keeping the height of hub 16 constant. These may include a belt or a chain that transmits yaw rotation between the posts 26.

In the discussion of the sensor 47 earlier herein, an advantage of the present invention was given as being that the post 49 always retained the same spacing between each of the wheels 13. The arrangement of FIG. 7 illustrates how this is achieved by the geared arrangement discussed. Of course other arrangements could be employed to achieve this same result, but the geared arrangement shown in FIG. 7 is simple and highly effective in achieving this result and beneficially, the result can be achieved even though only one of the four legs 15 is driven to rotate.

It will also be understood that the geared arrangement shown in FIG. 7 maintains the spacing between the wheels 13 constant, once the driven leg is driven to the desired position. Thus, until a leg 15 is driven further, all of the legs will retain the set angular relationship between them and not deviate from that position until the driven leg is driven further.

Figure 9:
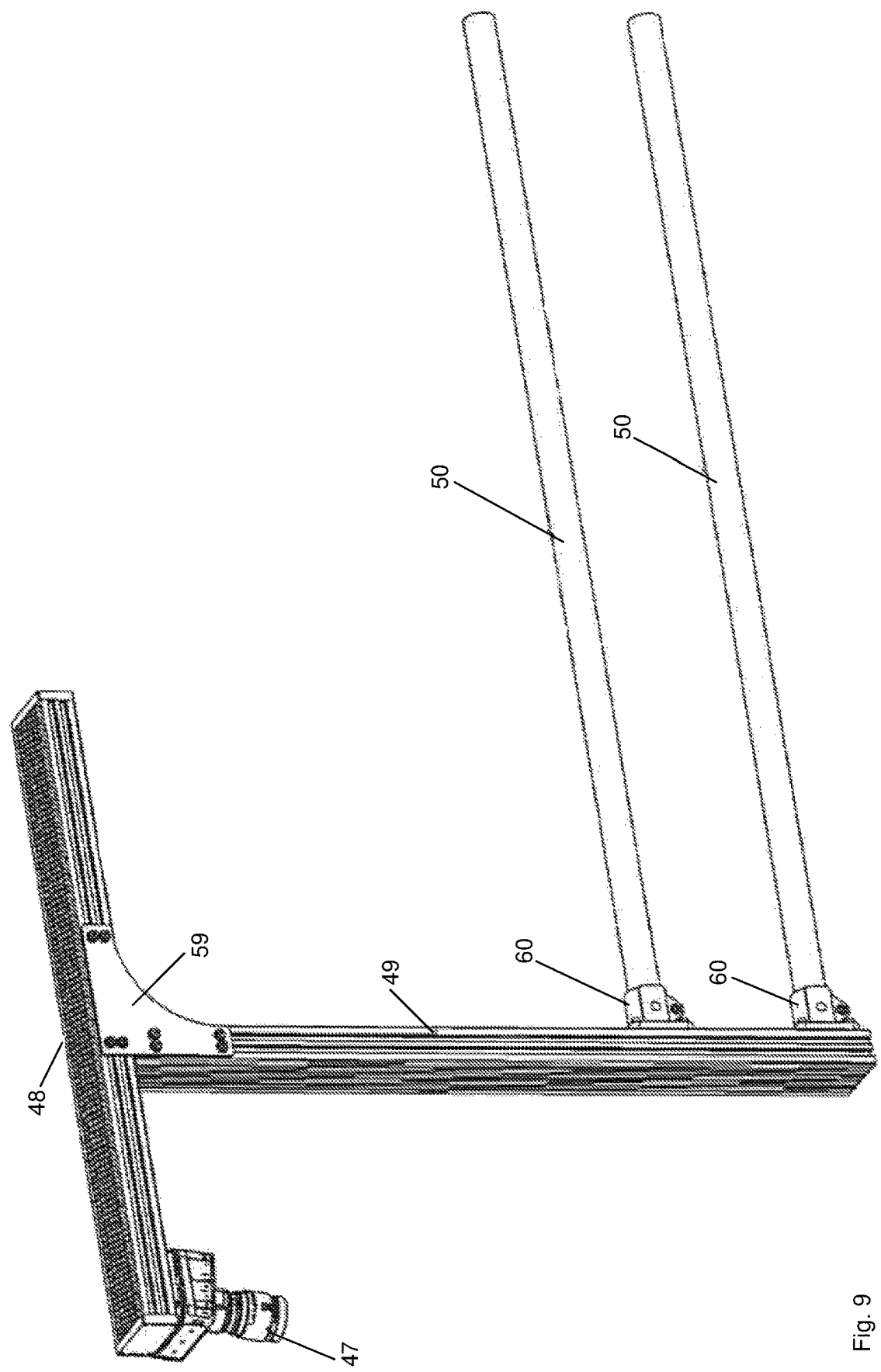
FIG. 9 is a view of a sensor mounting arrangement.

FIG. 9 illustrates the mounting arrangement for mounting the sensor 47 and shows in greater detail the leg 48, the post 49 and the rails 50. It can be seen from FIG. 9 that the plate 59 secures the leg 48 to the post 49, although the arrangement could alternatively be an adjustable arrangement, whereby the leg 48 could move forward and back relative to the post 49 and in fact there could be a rotatable adjustment, so that the leg 48 could rotate about the lengthwise axis of the post 49.

The post 49 can be moved vertically from the position shown in FIG. 9 to adjust the vertical height of the sensor 47. The rails 50 are mounted within a track on the post 49 and thus can be moved within the track and when the final position of the rails 50 relative to the post 49 has been achieved, clamps 60 can be tightened to secure the relative position of the rails to secure the relative position of the rails 50 relative to the post 49. In this manner, the height of the sensor 47 relative to that of hub 16 can be adjusted.

Figure 13:
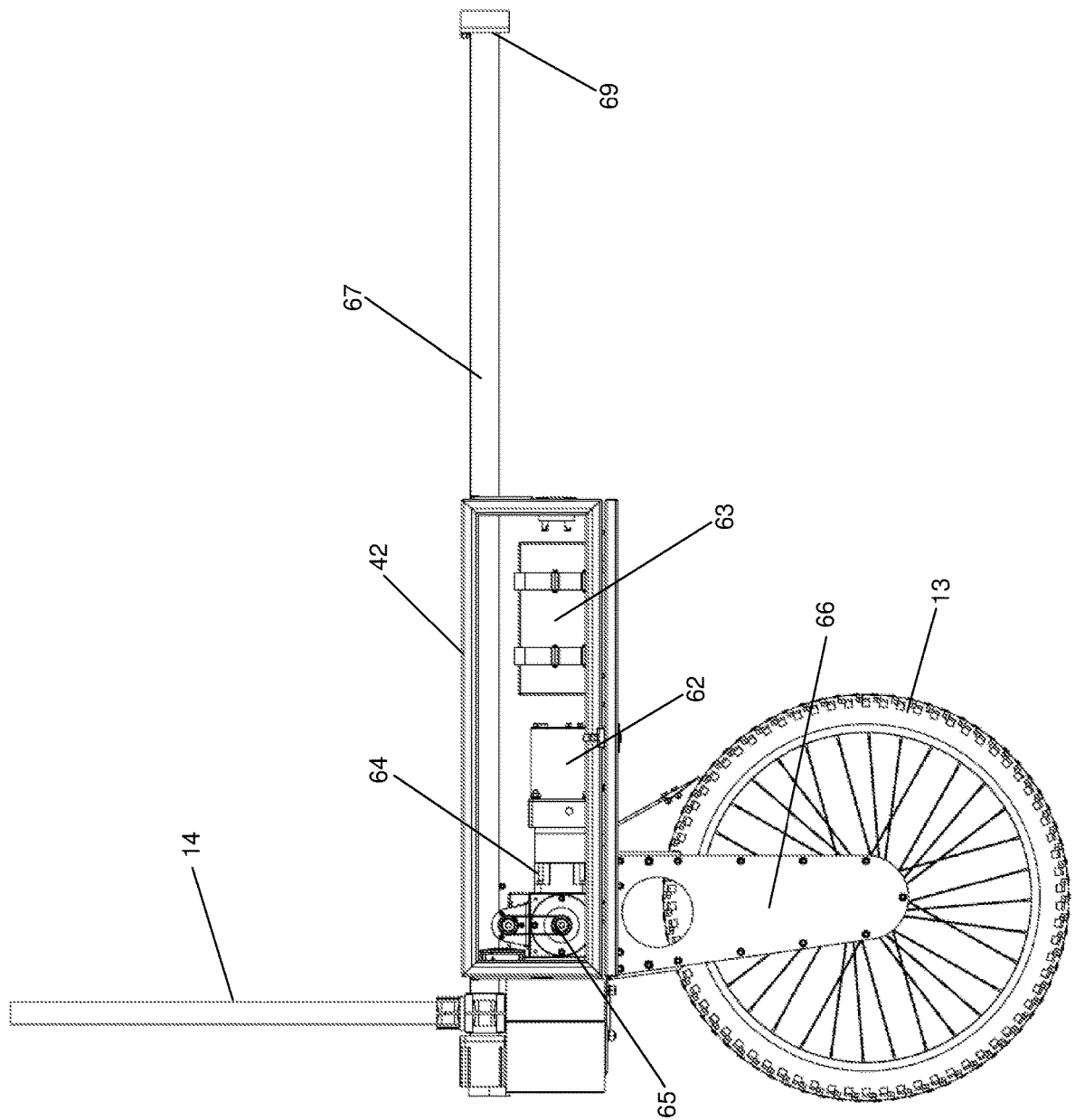
FIG. 13 is a side view of a wheel assembly of the vehicle of FIG. 2.

As indicated earlier, the entire mounting arrangement of FIG. 9 can be moved forward and backward relative to the hub 16 by movement of the rails 50 through the slide tubes 51 of the hub 16. While only a single sensor 47 is shown, it needs to be appreciated that the vehicle 10 could host or support a variety of sensors and it is intended that the lower structural body 19 be set up in order for additional sensors to be properly mounted. Sensors could for example extend from the hub 16 laterally to the rails 15 in order to take measurements to the side of the vehicle 10, while further sensors could be disposed on the ends of the rails 50 opposite to the post 49 for sensing different characteristics of the crop being analysed. Sensors could also be placed on or extend from the legs 15 and from the drive housings 42 for example. This discussion is to highlight that sensors or measuring equipment can be placed at any suitable position on the vehicle 10 for sensing or measuring various traits appropriate to the crop being analysed. Still further, the hub 16 or other structural elements of the vehicle 10 could support delivery systems for delivering fertiliser or other crop treatments where a particular deficiency is detected by the sensing equipment (the sensor 47 for example) and where a treatment product is available instantly via the vehicle 10. For example, the vehicle 10 could include a supply of a certain fertiliser and could include suitable spray or delivery equipment so that upon sensing a deficiency in the crop through the sensor 47, an immediate delivery of the fertiliser can be made at the point at which the deficiency is detected. In other examples, the vehicle 10 is used for weed detection and application of herbicide or automatic weed removal or pest detection and pesticide removal. FIG. 13 is a detailed view of one of the forward wheels 13 of the vehicle 10, which includes the drive housing 42, but it is shown open so that the interior components within the housing 42 are visible. FIG. 13 shows vehicle propulsion mechanism including a mover, such as a drive motor 62 which is powered by a battery 63. A clutch 64 is provided intermediate the drive motor 62 and a chain drive arrangement 65. The chain drive drives a gear sprocket which connects to the axle of the wheel 13, all of which are obscured by the chain cover 66. The drive arrangement illustrated in FIG. 13 is the same drive arrangement which is applied to each of the front wheels 13 and drive of the respective motors 62 allows the front wheels 13 to be driven at different speeds in order to steer the vehicle 10. Other examples of movers are combustion engines including diesel or petrol and tractors or other vehicles that tow or push vehicle 10.

The wheels 13 can be driven at different speed for steering and thus they can be fixed against rotation, or alternatively or in addition, one or more of the wheels 13 can be rotatable and steerable. In one example, one or both of the front wheels are driven, both of the rear wheels are rotatable and one of the rear wheels is arranged for manual steering. This advantageously enables the vehicle to be steered from behind as might be required in some phenotyping activities, but more likely, allow manual steering for moving the vehicle between different crops or onto and off a transport vehicle.

FIG. 13 further shows a hollow rod 67 extending rearwardly of the housing 42 and that rod 67 receives a further rod 68 (see FIG. 2) that extends to the rear wheel 13. A clamp 69 allows the relative positions of the rod 67 and rod 68 to be fixed and it will be appreciated that the rod 68 telescopically slides within the rod 67 once the clamp 69 has been released and during folding and unfolding movement of vehicle 10. Actuation of the clamp 69 is one of the few procedural steps in the transition of the vehicle 10 between folded and unfolded configurations and positions intermediate the folded and unfolded configurations but once the appropriate configuration has been achieved the clamps 69 on opposite sides of the vehicle 10 can be secured or tightened and that fixes the distance (wheelbase) L (FIG. 2) between the respective front and rear wheels 13.

In one example, vehicle 10 comprises a further actuator 91 that expands or contracts rod assembly 67,68. The further actuator 91 may be a worm drive actuator, pneumatic actuator or electric actuator. The actuator changes the length L between the front and rear wheels and as described above, this changes the track width W of the vehicle due to the mechanical coupling of the legs in hub 16. The advantage is that operator 12 can continuously adjust the track width to accommodate for varying row widths without affecting the symmetry of vehicle 10 or changing height of sensor 47. The actuator or parts of the actuator, such as an electric motor, may be located within housing 42.

It can be seen in FIG. 2 that the rear wheels 13 include a rotatable coupling 70 that connects between a suspension arm 71 and post 14 and allows the rear wheels 13 to swivel as required. In FIG. 2, it can be seen that the operator 12 has control of a steering rod 72 and this allows a manual steering of the vehicle 10. An interface 75 is also shown attached to a free end of the rod 72 and this can be used to provide information to the operator 12 for the purposes of assessing vehicle speed, vehicle position, battery levels, sensing data etc. It will be appreciated that while the figures show an operator 12 in position steering and controlling the movement of the vehicle 10, the vehicle 10 can alternatively be remotely controlled using GPS navigation or other control systems, to move autonomously. For example, controller 75 may maintain a constant speed based on the highly accurate relative position data provided by the wheel rotary encoders. There may also be a tractor or other mover to pull or push vehicle 10 and vehicle 10 may comprise suitable couplings for this application.

The encoders can for example be employed on the wheels to track speed, direction and distance. Encoders can dynamically and accurately identify the relative position of the vehicle in a field so that images or data that the sensor collects, such as a line scanner, can be compiled into an accurate image for later analysis. More particularly, for some applications it is important that the data from each line scan is associated with a relative location. One such application may be the calculation of a numerical value for biomass. Therefore, it is important that the distance travelled is accurately measured. In this sense, it is relatively less important that the absolute position is accurate because the calculated biomass does not significantly depend on the absolute position within the GPS reference, for example.

Figure 6B:
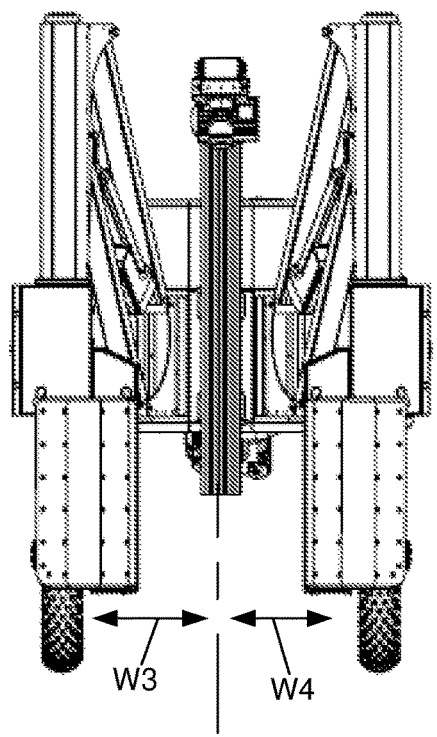
Figure 10A:
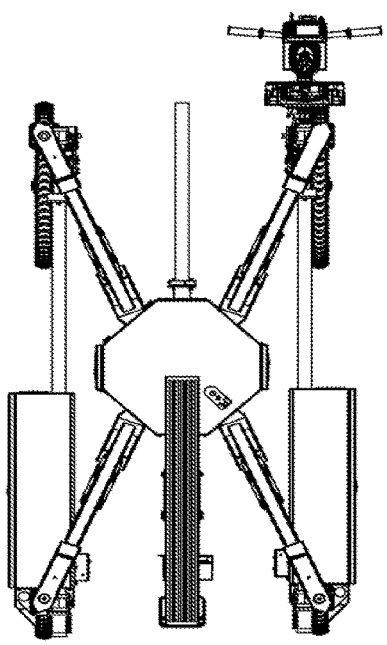

The collapsibility or foldability of the vehicle 10 has been described above as being of significant importance to the present invention. FIGS. 6a and 6b already show movement between the expanded and minimum folded configurations, while FIGS. 10a and b and 11a and b show plan and side views of the movement which is available in the vehicle 10. FIG. 10a shows a plan view of the vehicle 10 in a fully collapsed condition, while FIG. 10b shows the vehicle 10 in a fully expanded condition, in which the legs 15 have been rotated further beyond that shown in FIG. 7 to increase the angles α, β, ε and δ, so that the wheel track is further widened. FIG. 10b can be compared with the plan view of FIG. 7 to show the different angular positions of the legs 15 and the greater width W between the wheels 13. In the position of FIG. 10b, the clamps 69 have shifted (such as under control of an actuator) via the telescopic movement of the rod 68 into the rod 67 so that the clamps have moved into either close proximity or actual engagement with the coupling 70 of the rear wheels 13. At that point, no further rotation of the legs 15 in the direction of the arrow A of FIG. 10b can be made. Again however, it is noted that the spacing between the wheels 13 of the vehicle 10 and the leg 48 remains equal, so that symmetry of the vehicle remains constant despite rotation of the legs 15 to the maximum extended configuration.

Figure 11A:
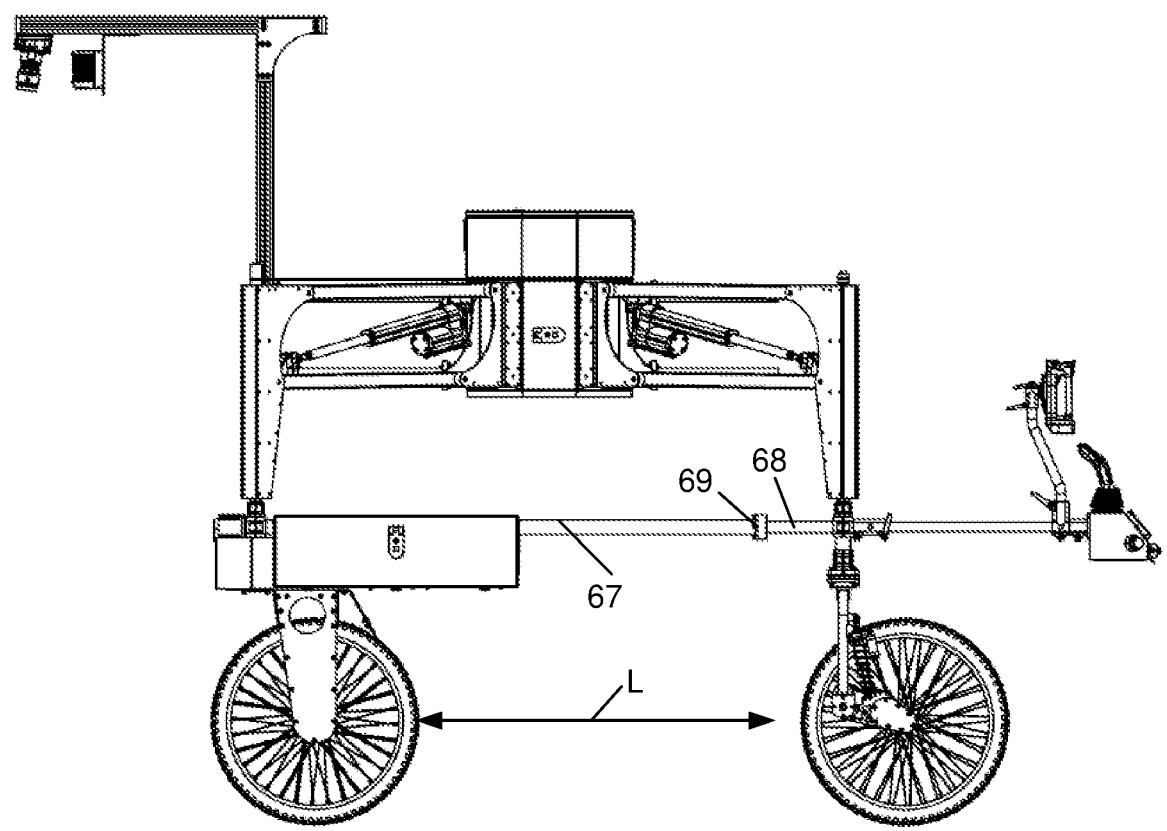
FIGS. 11a and 11b are side views of the vehicle of FIG. 2 in expanded and collapsed configurations respectively.
Figure 11B:
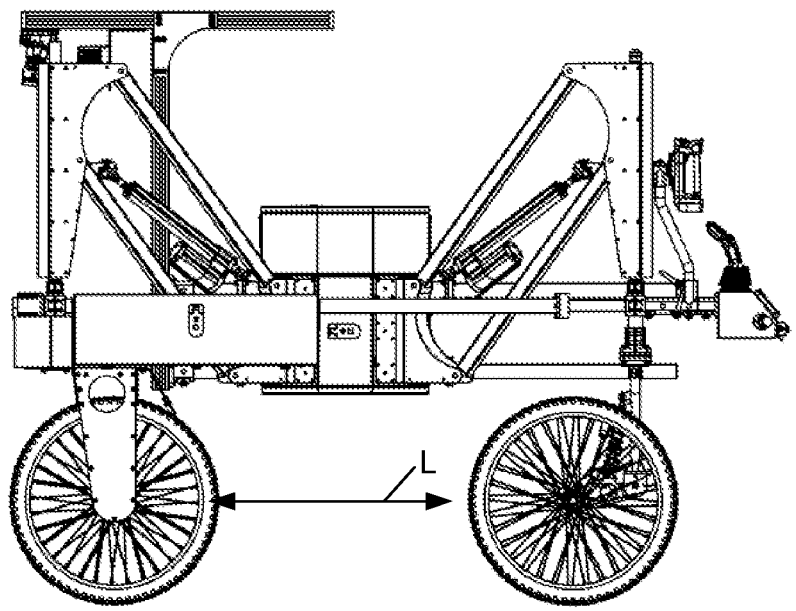

FIGS. 11a and 11b clearly show the change in length L that occurs between the expanded and collapsed configurations of FIGS. 2 and 5.

Figure 12:
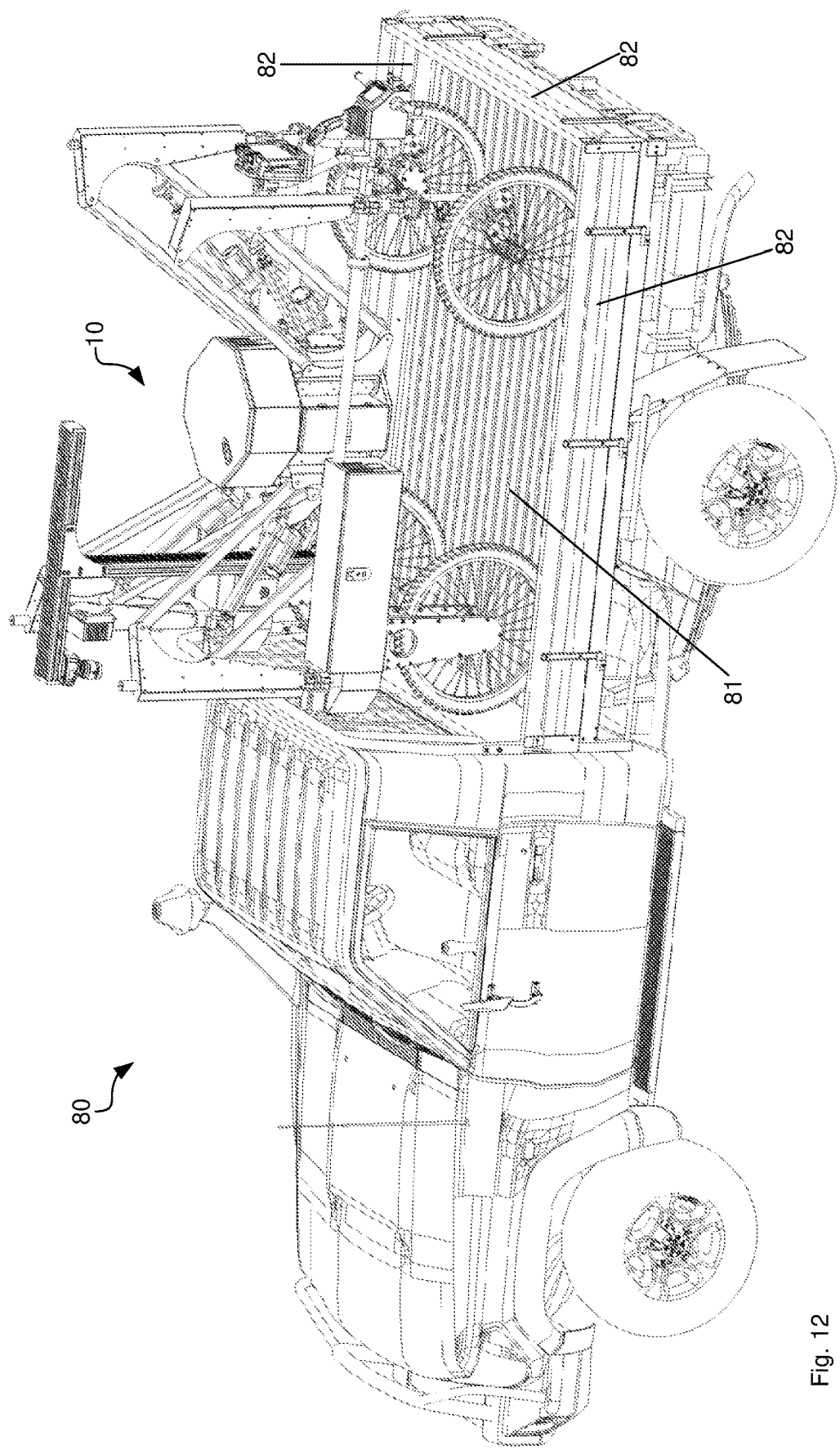
FIG. 12 is a perspective view of the vehicle of FIG. 2 loaded onto a utility vehicle.

A major advantage of the vehicle 10 of the present invention is that in the fully collapsed configuration, the vehicle 10 can convert to a size that is easily transportable on the tray of a utility vehicle 80 (see FIG. 12), or on a trailer or flatbed truck. FIG. 12 illustrates a standard utility vehicle with the vehicle 10 of the earlier Figures resting on the tray 81 and within the walls 82 of the vehicle 80. The ability to collapse to the minimum configuration shown in FIG. 13 enables ready and easy transport between different locations (different farms, or different crops within the same farm), and given that the vehicle 10 can fit onto a standard utility vehicle 80, and given that most if not all farms would have access to such a vehicle, no special equipment is required for the transporting process. This advantage, when combined with the significant expansion that the vehicle 10 can undergo to provide a wheel track width of about 2.8 m, is not available in other similar vehicles that are known to the inventors. Other vehicles that might be able to fit onto the tray of a utility vehicle do not provide the expansion that the vehicle of the present invention does, while vehicles that do provide such expansion do not fit onto a utility vehicle as shown.

As a further example, and in relation to field-based phenotyping, one aspect for achieving accurate and useful results is that position of the vehicle is accurately known at all times. In relation to line scanning, a scan of a crop can be taken each 3mm and many individual scans are merged together to create a two dimensional image. A laser scanner can also be used to provide depth to create a three dimensional image. Because the scan width is so small, the position of the vehicle, in particular the incremental position of the vehicle, is important to know at all times, so that the image that is created is created by line scans that are successive. Use of GPS on its own may not give sufficient accuracy, and so sensors such as encoders are applied to the wheels of the vehicle and those encoders communicate with each other to provide feedback as to where in a crop vehicle 10 is positioned. Calibration of the sensors that communicate with each other can be carried out once and not need further calibration even though the spacing between the various wheels of the front and rear wheels is modified or changed.

In addition to the advantages discussed above, the connection between the legs also facilitates very quick adjustment of the legs to increase or decrease the track width of the wheels or to transition the vehicle from the collapsed configuration for transport and the expanded configuration for field-based phenotyping. As one leg moves, all four legs are moved together so that separate movement of the legs is not required.

The body of the vehicle will usually be a central body, although that is not essential. It is most important for a vehicle in which the body forms the centre of gravity of the vehicle. It is however envisaged that in most forms of the invention, the body will be a central body as that provides advantages in the expansion and contraction of the vehicle that a non-central body would make more difficult.

While some examples described herein relate to centrally positioned sensors, the sensors do not need to be centrally positioned for the discussed benefits to arise. Other sensors can be positioned elsewhere on the vehicle and the benefit of symmetrical movement of the legs and wheels is retained, because algorithms can accommodate the changes of position given that the legs and wheels all move the same amount. It will be appreciated that the sensors can be any suitable sensor available in the art. Examples of such sensors include a portable x-ray to measure plant density, a multi-sterscopic RGB system for extracting morphometric quantification of plants, multi or hyperspectral camera for quantifying chemical of physiological plant status, fluorescence system for measuring photosynthetic parameters, light curtains for measuring plant height far infrared imaging to measure plant temperatures and water use or radiometirce sensors for measuring electromagnetic spectrum to quantify plant water status and temperature.

In the example where the central body forms the centre of gravity of the vehicle, the collapsible vehicle can advantageously provide improved stability particularly as used during plant scanning, for example phenotyping activities. In those activities, the vehicle is often driven over uneven ground and the ground can be inclined requiring the vehicle to travel uphill and downhill and to traverse across the incline. By the central body forming the centre of gravity of the vehicle, the vehicle is less likely to tip while sensors mounted to the central body will be more stable for better image or information capture. In terms of the weight of the vehicle, the central body preferably has a significant portion of the weight, for example about at least 50% of the weight.

Figure 14:
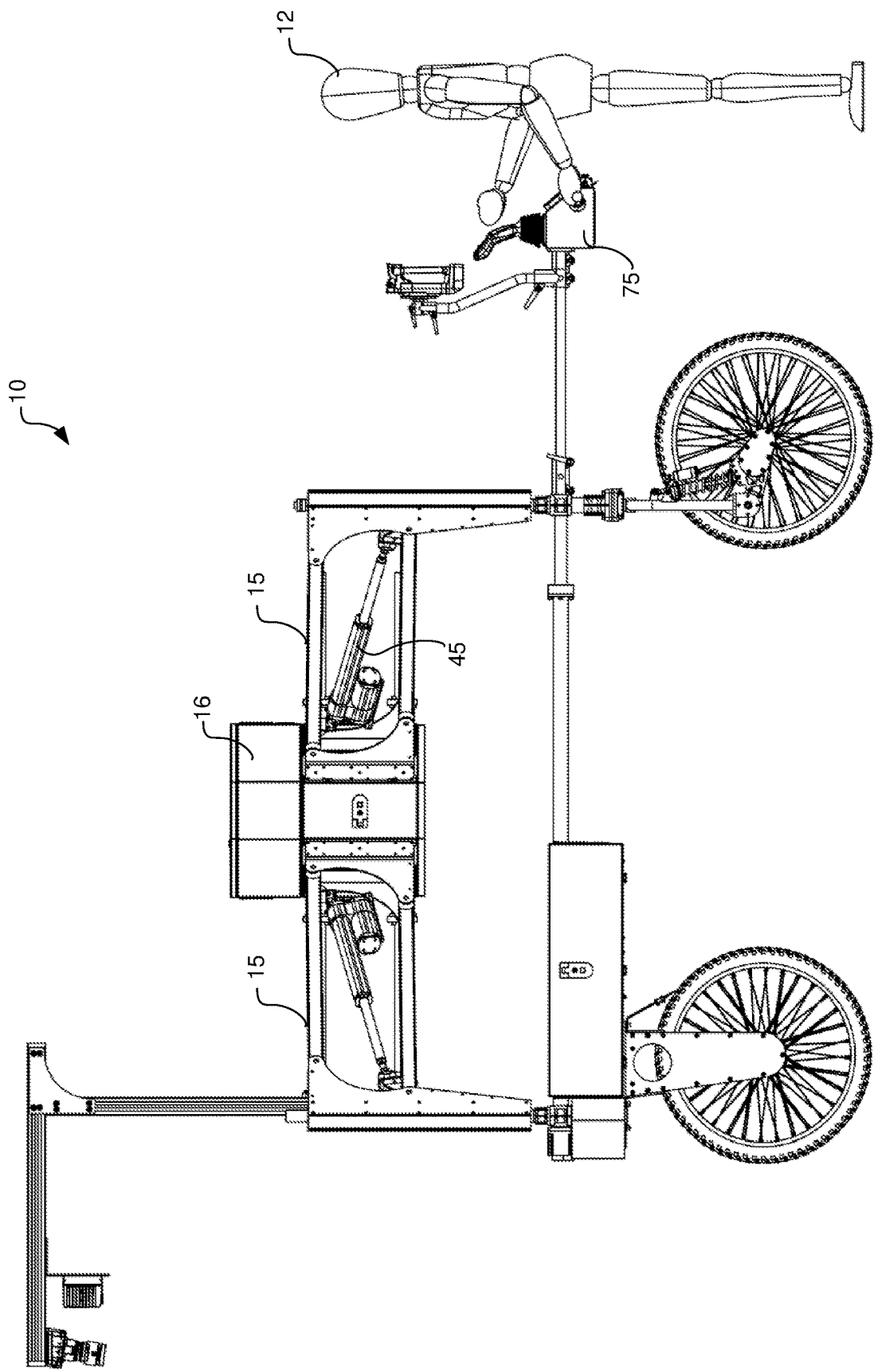
FIG. 14 is a side elevation view of the vehicle steered by an operator.

FIG. 14 is a side elevation view of vehicle 10 steered by operator 12. This view shows how the height of the central body is chosen such that the legs 15 are horizontal. In one example, when operator 12 directs the controller 75 to expand vehicle 10, controller 75 automatically controls the pneumatic actuators 45 to expand until the legs 15 are horizontal. Clamps 69 may either be released manually or automatically by controller 75 such that rods 67 and 68 slide freely in this operation. Operator 12 can then make further adjustments from this configuration to accommodate the particular crop height, for example. When the desired configuration is set-up, clamps 69 are fastened by the operator 12 or automatically.

Figure 15:
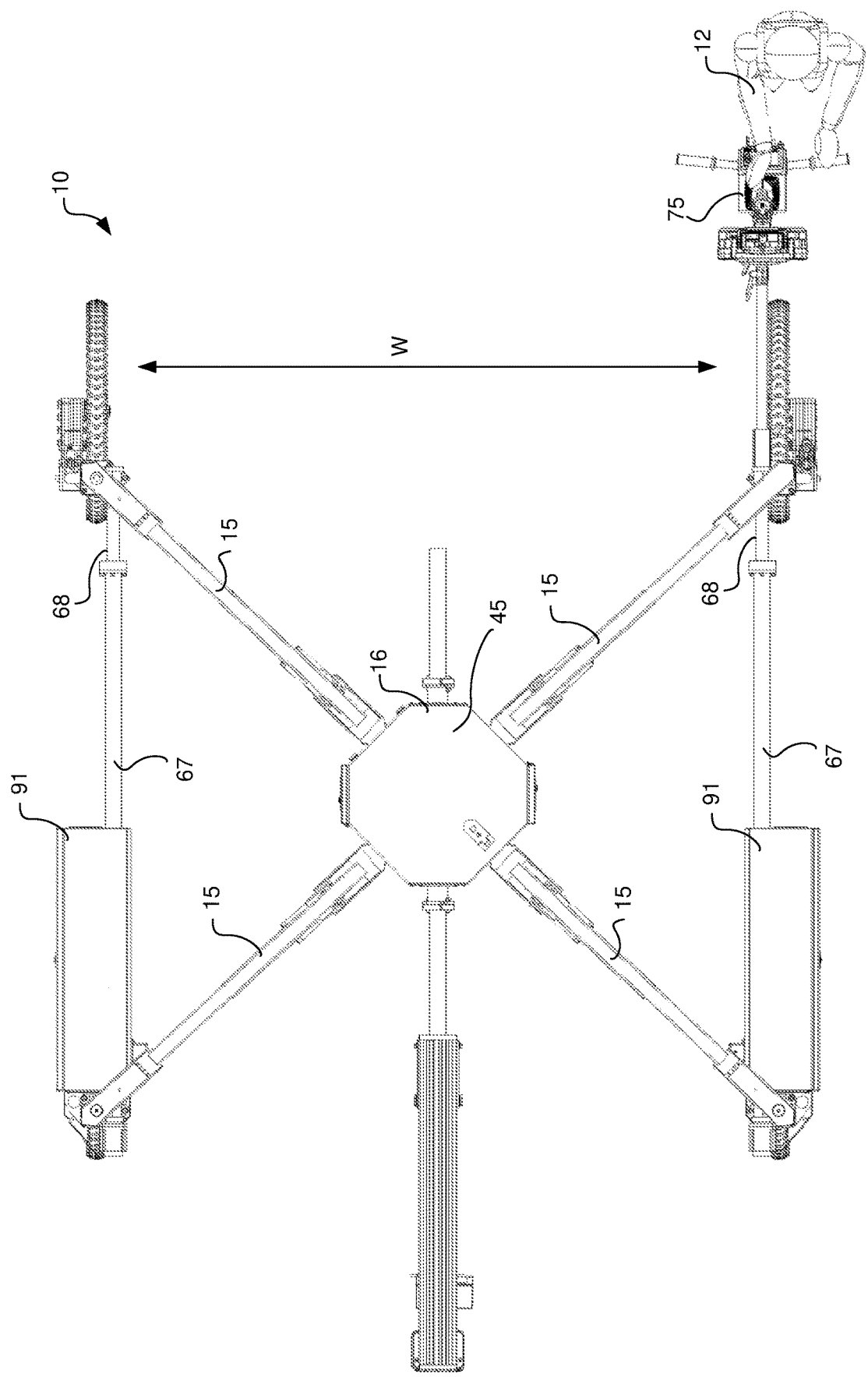
FIG. 15 is a plan view of the configuration in FIG. 14.

FIG. 15 is a plan view of the configuration in FIG. 14. As can be seen, there is an angle of about 90 degrees between any two legs 15. From this configuration, operator 12 can direct controller 75 to change the track width of vehicle 10. In turn, controller 75 controls second actuators (generally indicated at 91) to extend or retract connection member 67, 68 to change the distance between front and rear wheels and thereby change the track width. It is noted that only a single actuator 91 is necessary due to the mechanical coupling in hub 16 that transmits the rotation to the other legs. However, for extra rigidity a second actuator 91 is provided in this example. While the actuators 91 are provided between front and rear wheels, they may also be provided between left and right wheels. The advantage of having the actuators 91 between front and rear wheels is that they do not affect the clearance of vehicle 10. The actuators 91 may be used in combination with the arrangement using clamps 69 in the sense that clamps 69 can be loosened when the vehicle is collapsed/expanded and then the actuators 91 can be used to make adjustments to the track width. In that case, each clamp 69 may be replaced by bores through rods 67 and 68 that align at the expanded position so that a pin can be fed through the bores to lock the rods 67 and 68 in their relative position. In other examples, operator 12 can enter a desired track width and desired height and a controller, such as a remote control or on-board electronics, calculate the required length of the actuators to achieve the desired width and height and send control signals to the actuators to cause them to adjust accordingly.

Figure 16:
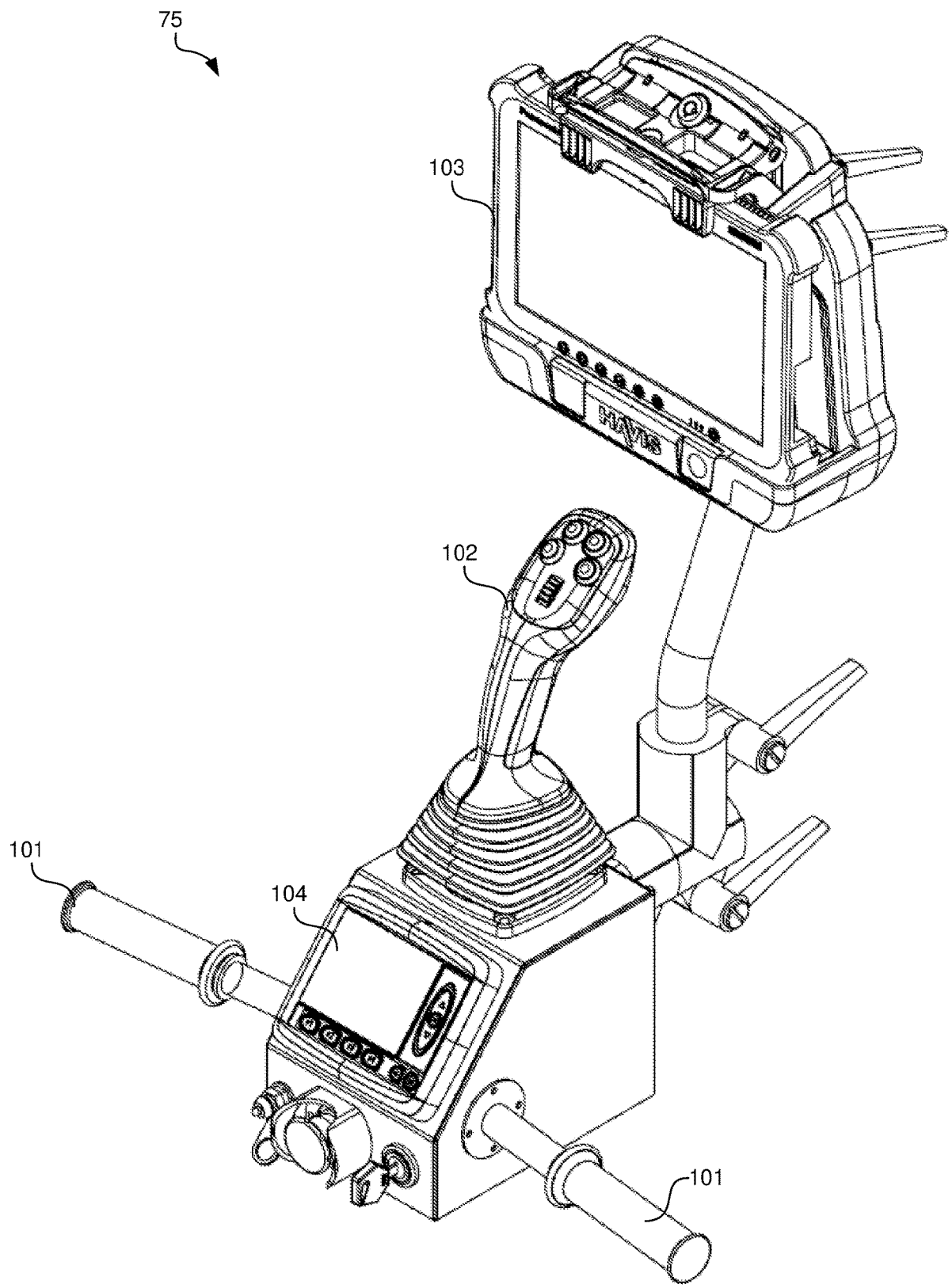
FIG. 16 illustrates a controller.

FIG. 16 illustrates controller 75 in more detail. Controller 75 comprises handles 101 so that operator 12 can securely grip and steer vehicle 10. There is also a joystick 102, a first display 103 and a second display 104. The joystick 102 can be used in the case of motorised propulsion and motorised steering. However, in other examples, vehicle 10 is pushed manually and steered manually. Second display 104 may show the current parameters of the vehicle configuration, such as body height and track width, which may also be adjustable via joystick 102 or by touching the display 103. First display 103 may show the current line scan in a side elevation view or a 3D/isometric view so that operator 12 can verify that the scanning takes place. Ideally, operator 12 would be able to recognise the ground on either end of the line scan as parts of the lowest plant height/greatest distance from the sensor. If operator 12 does not see the ground on either side of the scan, the track width may need to be widened. Conversely, if too much of the scan represents ground, the track width may need to be narrowed.

While some examples herein relate to crops, there are other plants that can equally be scanned, such as vines, trees or flowers, and other applications in horticulture and forestry. Further, while some examples herein relate to a vehicle with four legs, other example vehicles may have only three legs where one of the legs that support the rear wheels of the four-wheeled configuration is removed. In yet further examples, the vehicle may have six or eight wheels with half of the wheels on either side. In another example, the vehicle has tracks instead or in addition to wheels.

Throughout the description and claims of the specification, the word "comprise" and variations of the word, such as "comprising" and "comprises", is not intended to exclude other additives, components, integers or steps.

The invention described herein is susceptible to variations, modifications and/or additions other than those specifically described and it is to be understood that the invention includes all such variations, modifications and/or additions which fall within the spirit and scope of the present disclosure.

Future patent applications may be filed in Australia or overseas on the basis of or claiming priority from the present application. It is to be understood that the following provisional claims are provided by way of example only, and are not intended to limit the scope of what may be claimed in any such future applications. Features may be added to or omitted from the provisional claims at a later date so as to further define or re-define the invention or inventions.

The invention claimed is:

1. A plant scanning vehicle comprising:
a central body;
three or more legs extending from the central body to support a wheel on each leg;
wherein the three or more legs are mounted to the central body rotatably about a respective vertical axis to allow adjustment of a track width of the vehicle by rotating the legs wherein the legs are mechanically coupled to transmit rotation between the legs about their respective vertical axes and the central body or the three or more legs are configured to support a sensor to scan plants.

2. The plant scanning vehicle of claim 1, wherein the legs are mechanically coupled to maintain symmetry between the wheels and legs of the vehicle, and the body.

3. The plant scanning vehicle of claim 1, wherein the legs are mechanically coupled to cause the legs to rotate about the respective vertical axes by the same angle.

4. The plant scanning vehicle of claim 1, wherein the sensor is aligned with a centreline of the vehicle, the legs comprise two front wheels and the legs are mechanically coupled to maintain the alignment of the sensor and the centreline during movement of the two front wheels away from each other or towards each other.

5. The plant scanning vehicle of claim 1, wherein the legs have proximal ends at the central body and are coupled via a toothed coupling.

6. The plant scanning vehicle of claim 5, wherein the toothed coupling comprises a curved rack that is attached to the proximal end of each leg.

7. The plant scanning vehicle of claim 1, wherein
the three or more legs support a front wheel and a rear wheel,
the front wheel is connected to the rear wheel by a rigid member of variable length, and
reducing the length of the rigid member reduces the distance between the front wheel and the rear wheel.

8. The plant scanning vehicle of claim 7, wherein the rigid member comprises a first actuator to change the length of the rigid member to thereby adjust the track width.

9. The plant scanning vehicle of claim 8, wherein adjusting the track width by changing the length of the rigid member causes rotation of the legs about respective vertical axes and thereby maintains a constant height of the central body.

10. The plant scanning vehicle of claim 1, wherein the legs comprise one or more joints to allow rotation of the legs about a respective horizontal axis to adjust the height of the central body and/or to collapse the vehicle.

11. The plant scanning vehicle of claim 10, further comprising second actuators acting on the legs for rotating the legs upwardly and downwardly about the joints wherein upward rotation of the legs moves the legs towards a collapsed configuration and downward rotation of the legs moves the legs towards an expanded configuration.

12. The plant scanning vehicle of claim 1, wherein the legs are formed as parallelograms comprising a pair of parallel rods which connect at one end to the central body and at the other end to the wheels.

13. The plant scanning vehicle of claim 12, wherein second actuators are connected diagonally across the parallelograms so that contraction of the second actuators rotates the legs upwardly or downwardly and expansion of the second actuators rotates the legs in the opposite direction.

14. The plant scanning vehicle of claim 1, further comprising an adjustable sensor mount to mount the sensor to the central body, wherein the sensor mount is configured to move the sensor in the direction of travel or adjust the height of the sensor or both.

15. The plant scanning vehicle of claim 1, wherein the sensor is a laser scanner to measure a distance of the plants from the sensor.

16. The plant scanning vehicle of claim 1, further comprising a rotary encoder applied to the wheels of the vehicle to provide relative location data of the vehicle.

17. The plant scanning vehicle of claim 1, further comprising a mover to propel the vehicle.

18. The plant scanning vehicle of claim 1, wherein one or more of the wheels are rotatable about a vertical axis to steer the vehicle.

19. The plant scanning vehicle of claim 1, further comprising control electronics to determine control signals for actuators based on user input.

20. The plant scanning vehicle of claim 19, wherein the user input indicates a desired height of the central body or a desired track width or both.

* * * * *